United States Patent
Harvey et al.

(10) Patent No.: US 7,375,258 B2
(45) Date of Patent: *May 20, 2008

(54) TRANSGENIC AVIANS WITH AN OVOMUCOID GENE EXPRESSION CONTROL REGION LINKED TO A NUCLEOTIDE SEQUENCE ENCODING A HETEROLOGOUS POLYPEPTIDE

(75) Inventors: Alex J. Harvey, Athens, GA (US); Youliang Wang, Monroe, GA (US)

(73) Assignee: AviGenics, Inc., Athens, GA (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/496,731

(22) PCT Filed: Dec. 2, 2002

(86) PCT No.: PCT/US02/38413

§ 371 (c)(1),
(2), (4) Date: May 21, 2004

(87) PCT Pub. No.: WO03/048364

PCT Pub. Date: Jun. 12, 2003

(65) Prior Publication Data

US 2005/0050581 A1  Mar. 3, 2005

Related U.S. Application Data

(63) Continuation-in-part of application No. 09/998,716, filed on Nov. 30, 2001, now Pat. No. 6,875,588.

(51) Int. Cl.
*A01K 67/027* (2006.01)
*C12N 15/00* (2006.01)

(52) U.S. Cl. .......................................... 800/19; 800/21
(58) Field of Classification Search ................. 800/19, 800/21
See application file for complete search history.

(56) References Cited

U.S. PATENT DOCUMENTS

| | | | |
|---|---|---|---|
| 4,237,224 | A | 12/1980 | Cohen et al. |
| 4,603,112 | A | 7/1986 | Paoletti et al. |
| 4,722,848 | A | 2/1988 | Paoletti et al. |
| 4,769,330 | A | 9/1988 | Paoletti et al. |
| 5,174,993 | A | 12/1992 | Paoletti et al. |
| 5,175,384 | A | 12/1992 | Krimpenfort et al. |
| 5,338,683 | A | 8/1994 | Paoletti et al. |
| 5,494,807 | A | 2/1996 | Paoletti et al. |
| 5,505,941 | A | 4/1996 | Paoletti et al. |
| 5,580,859 | A | 12/1996 | Felgner et al. |
| 5,589,466 | A | 12/1996 | Felgner et al. |
| 5,591,639 | A | 1/1997 | Bebbington |
| 6,825,396 | B2 * | 11/2004 | MacArthur .................. 800/19 |

FOREIGN PATENT DOCUMENTS

| | | |
|---|---|---|
| WO | WO 92/06180 | 10/1990 |
| WO | WO 92/19749 | 5/1991 |
| WO | WO 92/20316 | 5/1991 |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |
| WO | WO 97/47739 | * 12/1997 |

OTHER PUBLICATIONS

On-line Medical Dictionary definition of "transgenic".*
Vick, Proc. R. Soc. Lond., 1993, vol. 251, p. 179-182.*
Love (Bio/Technology, 1994, vol. 12, p. 60-63).*
Tanaka (1994, J. Reprod. Fert., vol. 100, p. 447-449).*
Thoraval (Transgenic Research, 1995, vol. 4, p. 369-376.*
Naito ("The Microinjeciton of DNA into early chicken embryo," Transgenic Animals: Generation and Use, 1997, Ed. By Louis Marie Houdebine, Harwood Academic Publishers, p. 69-73).*
Mohammed (1998, Immunotechnology, vol. 4, p. 115-125).*
Sayegh (Dec. 15, 1999, vol. 72, p. 31-37).*
Proudman, 2001, "The quest for transgenic poultry: birds are not mice with feathers" Biotechnology in Animal Husbandry, vol. 5, Kluwer Academic Publishers, p. 283-299; p. 284, lines 1-6.*
Mizuarai (Biochemical and Biophysical Res. Comm. Aug. 24, 2001, vol. 286, p. 456-463).*
On-line Medical Dictionary definition of "transgenic" no date.*
Ishida (2002, Cloning Stem Cells, vol. 4, p. 91-102).*
Harvey (Nature Biotech, Apr. 2002, vol. 19, p. 396-399).*
Ivarie (Trends in Biotechnology, Jan. 2003, vol. 21, p. 14-19).*
Table of Bird Classification/Families of the Eastern US Birds no date.*
Molecular Structure and Flanking Nucleotide Sequences of the Natural Chicken Ovomucoid Gene,*Lai et al*; Cell 18:829-842 (Nov. 1979).
DNA methylation: organ specific variations in the methylation pattern within and around ovalbumin and other chicken genes, *Mandel et al*; Nucleic Acids Research 7:2081-2103(1979).

(Continued)

*Primary Examiner*—Michael Wilson
(74) *Attorney, Agent, or Firm*—Kyle D. Yesland

(57) ABSTRACT

The present invention provides novel isolated nucleic acids that comprise an avian nucleic acid sequence comprising a ovomucoid gene expression control region. The ovomucoid promoter region of the present invention will allow expression of an operably linked heterologous nucleic acid insert in a transfected avian cell such as, for example, an oviduct cell. The isolated avian ovomucoid of the present invention may be operably linked with a selected nucleic acid insert, wherein the nucleic acid insert encodes a polypeptide desired to be expressed in a transfected cell. The recombinant DNA of the present invention may further comprise a polyadenylation signal sequence. The present invention further includes expression vectors comprising an isolated avian ovomucoid gene expression control region of the present invention, and transfected cells and transgenic avians comprising the expression vectors.

12 Claims, 10 Drawing Sheets

OTHER PUBLICATIONS

Ovoinhibitor Introns Specify Functional Domains as in the Related and Linked Ovomucoid Gene, *Scott et al*; Journal of Biol. Chemistry, 262:5899-5907(1987).

Deoxyribonuclease I Sensitivity of the Ovomucoid-Ovoinhibitor Gene Complex in Oviduct Nuclei and Relative Location of CR1 Repetitive Sequences, *Scott et al*; Biochemistry 26:6831-6840 (1987).

Isolation and characterization of the chicken ovomucoid gene, *Lindenmaier et al*; Nucleic Acids Research, 7:1221-1232 (1979).

The chick ovomucoid gene contains at least six intervening sequences, *Catterall et al*; Nature 278:323-327 (Mar. 1979).

Effect of Estrogen on Gene Expression In the Chick Oviduct. Regulation of the Ovomucoid Gene, *Tsai et al*; Biochemistry 17:5773-5780 (1978).

Identification of potential ovomucoid mRNA precursors in chick oviduct nuclei, *Nordstrom et al*; Nature 278:328-331 (Mar. 1979).

mRNA Complexity and Egg White Protein mRNA Content in Mature and Hormone-Withdrawn Oviduct, *Hynes et al*; Cell 11:923-932 (Aug. 1977).

Multiple Initiation and Polyadenylation Sites for the Chicken Ovomucoid Transcription Unit, *Gerlinger et al*; J. Mol. Biol. vol. 162, p. 345-364 (1982).

* cited by examiner

| | | |
|---|---|---|
| OVINs1: | GGGAAACAATCTGCCTTGCA | SEQ ID NO: 3 |
| OVINs2: | TAGGCAGAGCAATAGGACTCTCAACCTCGT | SEQ ID NO: 1 |
| OVINs4: | AGATGAGGTGGATGGTTTAC | SEQ ID NO: 7 |
| OVINs5: | CAGCTTCTGCTAGCGTAGGT | SEQ ID NO: 8 |
| OVINs6: | ACGTGAACTCAAAGAGGCAC | SEQ ID NO: 9 |
| OVINs7: | ATCTCCTGAGCTCGGTGCTT | SEQ ID NO: 10 |
| OVINs8: | ACGAGGTTCCATGTCTTTCA | SEQ ID NO: 11 |
| OVMUa1: | AAGCCACAAAGCACGAAAGAG | SEQ ID NO: 4 |
| OVMUa2: | AAGCTTCTGCAGCACTCTGGGAGTTACTCA | SEQ ID NO: 2 |
| OVMUa3: | TAAATAGCACAGAACGCTGAGGGGAGTAAGG | SEQ ID NO: 12 |
| OVMUa4: | GAAGAGCTTGGTAGAAGACT | SEQ ID NO: 13 |
| OVMUa5: | ATGGAAATATGGGTTTCCTTC | SEQ ID NO: 14 |
| OVMUa6: | GCAGCTTATGGCTAATCGCT | SEQ ID NO: 15 |
| OVMUa7: | AGTGACCACTATCTGACCTG | SEQ ID NO: 16 |
| OVMUa8: | TAATCAGGAAGGCACACAGC | SEQ ID NO: 17 |
| OVMUP4.7.1: | AGATCTGGAGCAGCACTTGT | SEQ ID NO: 18 |
| OVMUP4.7.2: | AGCATGAAGTTCCTCACCCA | SEQ ID NO: 19 |
| OVMUP4.7.3: | ATGGAGAGGAATATTCCCTT | SEQ ID NO: 20 |
| OVMUP4.7.4: | ATTTCTCCAGGCGTGTGG | SEQ ID NO: 21 |
| OVMUP5.5.1: | ATTTCTCCAGGCGTGTGG | SEQ ID NO: 22 |
| OVMUP5.5.2: | ATGCGAGTGAAGGAGAGTTC | SEQ ID NO: 23 |
| OVMUP5.5.3: | GCAGCACGTGTAAGCTTGTA | SEQ ID NO: 24 |
| OVMUP5.5.4: | CAAGGCAAATTATCAGCAGA | SEQ ID NO: 25 |
| OVMUa9: | AAATGAAGCCGGCTGTTTTC | SEQ ID NO: 27 |
| OVINs9 | CTCTCAGCCACTCTGAACAA | SEQ ID NO: 28 |

FIG. 3

```
TAGGCAGAGCAATAGGACTCTCAACCTCGTGAGTATGGCAGCATGTTAACTCTGCACTGG    60
          OVOINHIBITOR 3' UNTRANSLATED REGION
AGTCCAGCGTGGGAAACAATCTGCCTTGCACATGAGTCTTCGTGGGCCAATATTCCCCAA
          OVOINHIBITOR 3' UNTRANSLATED REGION
CGGTTTTCCTTCAGCTTGTCTTGTCTCCTAAGCTCTCAAAACACCTTTTTGGTGAATAAA
          OVOINHIBITOR 3' UNTRANSLATED REGION
CTCACTTGGCAACGTTTATCTGTCTTACCTTAGTGTCACGTTTCATCCCTATTCCCCTTT

CTCCTCCTCCGTGTGGTACACAGTGGTGCACACTGGTTCTTCTGTTGATGTTCTGCTCTG..300
ACAGCCAATGTGGGTAAAGTTCTTCCTGCCACGTGTCTGTGTTGTTTTCACTTCAAAAAG
GGCCCTGGGCTCCCCTTGGAGCTCTCAGGCATTTCCTTAATCATCACAGTCACGCTGGCA
GGATTAGTCCCTCCTAAACCTTAGAATGACCTGAACGTGTGCTCCCTCTTTGTAGTCAGT
GCAGGGAGACGTTTGCCTCAAGATCAGGGTCCATCTCACCCACAGGGCCATTCCCAAGAT
GAGGTGGATGGTTTACTCTCACAAAAAGTTTTCTTATGTTTGGCTAGAAAGGAGAACTCA  600
CTGCCTACCTGTGAATTCCCCTAGTCCTGGTTCTGCTGCCACTGCTGCCTGTGCAGCCTG
TCCCATGGAGGGGCAGCAACTGCTGTCACAAAGGTGATCCCACCCTGTCTCCACTGAAA
TGACCTCAGTGCCACGTGTTGTATAGGGTATAAAGTACGGGAGGGGGATGCCCGGCTCCC
TTCAGGGTTGCAGAGCAGAAGTGTCTGTATAGAGTGTGTCTTAATCTATTAATGTAAC
AGAACAACTTCAGTCCTAGTGTTTTGTGGGCTGGAATTGCCCATGTGGTAGGGACAGGCC  900
TGCTAAATCACTGCAATCGCCTATGTTCTGAAGGTATTTGGGAAAGAAAGGGATTTGGGG
GATTGCCTGTGATTGGCTTTAATTGAATGGCAAATCACAGGAAAGCAGTTCTGCTCAACA
GTTGGTTGTTTCAGCCAATTCTTGCAGCCAAAGAGCCGGGTGCCCAGCGATATAATAGTT
GTCACTTGTGTCTGTATGGATGACAGGGAGGTAGGGTGACCTGAGGACCACCCTCCAGCT
TCTGCTAGCGTAGGTACAGTCACCACCTCCAGCTCCACACGAGTCCCATCGTGGTTTACC 1200
AAAGAAACACAATTATTTGGACCAGTTTGGAAAGTCACCCGCTGAATTGTGAGGCTAGAT
TAATAGAGCTGAAGAGCAAATGTTCCCAACTTGGAGATACTAGTTGGTATTAGTATCAGA
GGAACAGGGCCATAGCACCTCCATGCTATTAGATTCCGGCTGGCATGTACTTTTCAAGAT
GATTTGTAACTAACAATGGCTTATTGTGCTTGTCTTAAGTCTGTGTCCTAATGTAAATGT
TCCTTTGGTTTATATAACCTTCTTGCCATTTGCTCTTCAGGTGTTCTTGCAGAACACTGG 1500
CTGCTTTAATCTAGTTTAACTGTTGCTTGATTATTCTTAGGGATAAGATCTGAATAAACT
TTTTGTGGCTTTGGCAGACTTTAGCTTGGGCTTAGCTCCCACATTAGCTTTTGCTGCCTT
TTCTGTGAAGCTATCAAGATCCTACTCAATGACATTAGCTGGGTGCAGGTGTACCAAATC
CTGCTCTGTGGAACACATTGTCTGATGATACCGAAGGCAAACGTGAACTCAAAGAGGCAC
AGAGTTAAGAAGAAGTCTGTGCAATTCAGAGGAAAAGCCAAAGTGGCCATTAGACACACT 1800
TTCCATGCAGCATTTGCCAGTAGGTTTCATATAAAACTACAAAATGGAATAAACCACTAC
AAATGGGAAAAGCCTGATACTAGAATTTAAATATTCACCCAGGCTCAAGGGGTGTTTCAT
GGAGTAATATCACTCTATAAAGTAGGGCAGCCAATTATTCACAGACAAAGCTTTTTTTT
TTCTGTGCTGCAGTGCTGTTTTTCGGCTGATCCAGGGTTACTTATTGTGGGTCTGAGAGC
TGAATGATTTCTCCTTGTGTCATGTTGGTGAAGGAGATATGGCCAGGGGGAGATGAGCAT 2100
GTTCAAGAGGAAACGTTGCATTTTGGTGGCTTGGGAGAAAGGTAGAACGATATCAGGTCC
ATAGTGTCACTAAGAGATCTGAAGGATGGTTTTACAGAACAGTTGACTTGGCTGGGTGCA
GGCTTGGCTGTAAATGGATGGAAGGATGGACAGATGGGTGGACAGAGATTTCTGTGCAGG
AGATCATCTCCTGAGCTCGGTGCTTGACAGACTGCAGATCCATCCCATAACCTTCTCCAG
CATGAGAGCGCGGGGAGCTTTGGTACTGTTCAGTCTGCTGCTTGTTGCTTCCTGGGTGCA 2400
CAGTGGTGATTTTCTTACTCACACAGGGCAAAAACCTGAGCAGCTTCAAAGTGAACAGGT
TGCTCTCATAGGCCATTCAGTTGTCAAGATGAGGTTTTTGGTTTCTTGTTTTGTAAGGTG
GGAAGAAGCACTGAAGGATCAGTTGCGAGGGCAGGGGTTTAGCACTGTTCAGAGAAGTCT
TATTTTAACTCCTCTCATGAACAAAAGAGATGCAGGTGCAGATTCTGGCAAGCATGCAG
TGAAGGAGAAAGCCCTGAATTTCTGATATATGTGCAATGTTGGGCACCTAACATTCCCCG 2700
CTGAAGCACAGCAGCTCCAGCTCCATGCAGTACTCACAGCTGGTGCAGCCCTCGGCTCCA
```

FIG. 4a

```
GGGTCTGAGCAGTGCTGGGACTCACGAGGTTCCATGTCTTTCACACTGATAATGGTCCAA
                              CR1
TTTCTGGAATGGGTGCCCATCCTTGGAGGTCCCCAAGGCCAGGCTGGCTGCGTCTCCGAG
                              CR1
CAGCCCGATCTGGTGGTGAGTAGCCAGCCCATGGCAGGAGTTAGAGCCTGATGGTCTTTA
                              CR1
AGGTCCCTTCCAACCTAAGCCATCCTACGATTCTAGGAATCATGACTTGTGAGTGTGTAT 3000
                              CR1
TGCAGAGGCAATATTTTAAAGTTATAAATGTTTTCTCCCCTTCCTTGTTTGTCAAAGTTA
         CR1
TCTTGATCGCCTTATCAATGCTTTTGGAGTCTCCAGTCATTTTTCTTACAMCAAAAAGAG
GAGGAAGAATGAAGAGAATCATTTAATTTCTTGATTGAATAGTAGGATTCAGAAAGCTGT
ACGTAATGCCGTCTCTTTGTATCGAGCTGTAAGGTTTCTCATCATTTATCAGCGTGGTAC
ATATCAGCACTTTTCCATCTGATGTGGAAAAAAAAATCCTTATCATCTACAGTCTCTGTA 3300
CCTAAACATCGCTCAGACTCTTTACCAAAAAGCTATAGGTTTTAAAACTACATCTGCTG
ATAATTTGCCTTGTTTTAGCTCTTCTTCCATATGCTGCGTTTGTGAGAGGTGCGTGGATG
GGCCTAAACTCTCAGCTGCTGAGCTTGATGGGTGCTTAAGAATGAAGCACTCACTGCTGA
AACTGTTTTCATTTCACAGGAATGTTTTAGTGGCATTGTTTTATAACTACATATTCCTC
AGATAAATGAAATCCAGAAATAATTATGCAAACTCACTGCATCCGTTGCACAGGTCTTTA 3600
TCTGCTAGCAAAGGAAATAATTTGGGGATGGCAAAAACATTCCTTCAGACATCTATATTT
AAAGGAATATAATCCTGGTACCCACCCACTTCATCCCTCATTATGTTCACACTCAGAGAT
ACTCATTCTCTTGTTGTTATCATTTGATAGCGTTTTCTTTGGTTCTTTGCCACGCTCTGG
GCTATGGCTGCACGCTCTGCACTGATCAGCAAGTAGATGCGAGGGAAGCAGCAGTGAGAG
GGGCTGCCCTCAGCTGGCACCCAGCCGCTCAGCCTAGGAGGGGACCTTGCCTTTCCACCA 3900
GCTGAGGTGCAGCCCTACAAGCTTACACGTGCTGCGAGCAGGTGAGCAAAGGGAGTCTTC
ATGGTGTGTTTCTTGCTGCCCGGAAGCAAAACTTTACTTTCATTCATTCCCCTTGAAGAA
TGAGGAATGTTTGGAAACGGACTGCTTTACGTTCAATTTCTCTCTTCCCTTTAAGGCTCA
GCCAGGGGCCATTGCTGAGGACGGCATCGGGGCCCCTGGACCAAATCTGTGGCACAGAT
GGTTTCACTTACATCAGTGGATGTGGGATCTGCGCCTGTAATGTGTCCTTCTGAAGGAAG 4200
GAACGTGCCTTCCAAGTGCCAGCCCCACAGCCCCCAGCCCCTCCCTGTGCTGCTCCAATT
CATCTCCTCTTCCTCCTTCTCCCTTTGCTGTTTGTGCTCGGGTAGAAATCATGAAGATTT
AGAAGAGAAAACAAAATAACTGGAGTGGAAACCCAGGTGATGCAGTTCATTCAGCTGTCA
TAGGTTTGTCGTTGCTATAGGTCTGTATCAGAGATGCTARCACCACTTTGCTGTCGGTGC
TTAACTCGGGTGAACTCTCCTTCACTCGCATCATTTGCGGGCCTTATTTACATCCCCAGC 4500
ATCCATCACCCTCTGGGAAAATGGGCGCACTGGATCTCTAATGGAAGACTTTCCCTCTTT
CAGAGCCTGTGGGATGTGCAGTGACAAGAAACGTGGAGGGGCTGAGCAGCAGCACTGCCC
CCAGGGAGCAGGAGCGGATGCCATCGGTGGCAGCATCCCAAATGATGTCAGCGGATGCTG
AGCAGGCAGCGGACGAACGGACAGAAGCGATGCGTACACCTTCTGTTGACATGGTATTTG
GCAGCGATTTAACACTCGCTTCCTAGTCCTGCTATTCTCCACAGGCTGCATTCAAATGAA 4800
CGAAGGGAAGGGAGGCAAAAAGATGCAAAATCCGAGACAAGCAGCAGAAATATTTCTTCG
CTACGGAAGCGTGCGCAAACAACCTTCTCCAACAGCACCAGAAGAGCACAGCGTAACCTT
TTTCAAGACCAGAAAAGGAAATTCACAAAGCCTCTGTGGATACCAGCGCGTTCAGCTCTC
CTGATAGCAGATTTCTTGTCAGGTTGCGAATGGGGTATGGTGCCAGGAGGTGCAGGGACC
ATATGATCATATACAGCACAGCAGTCATTGTGCATGTATTAATATATATTGAGTAGCAGT 5100
GTTACTTTGCCAAAGCAATAGTTCAGAGATGAGTCCTGCTGCATACCTCTATCTTAAAAC
TAACTTATAAATAGTAAAACCTTCTCAGTTCAGCCACGTGCTCCTCTCTGTCAGCACCAA
TGGTGCTTCGCCTGCACCCAGCTGCAAGGAATCAGCCCGTGATCTCATTAACACTCAGCT
CTGCAGGATAAATTAGATTGTTCCACTCTCTTTTGTTGTTAATTACGACGGAACAATTGT
TCAGTGCTGATGGTCCTAATTGTCAGCTACAGAAACGTCTCCATGCAGTTCCTTCTGCG 5400
CCAGCAAACTGTCCAGGCTATAGCACCGTGATGCATGCTACCTCTCACTCCATCCTTCTT
```

FIG. 4b

```
CTCTTTCCCACCAGGGAGAGCTGTGTGTTTTCACTCTCAGCCACTCTGAACAATACCAAA
CTGCTACGCACTGCCTCCCTCGGAAAGAGAATCCCCTTGTTGCTTTTTTATTTACAGGAT
CCTTCTTAAAAAGCAGACCATCATTCACTGCAAACCCAGAGCTTCATGCCTCTCCTTCCA
CAACCGAAAACAGCCGGCTTCATTTGTCTTTTTTAAATGCTGTTTTCCAGGTGAATTTTG  5700
GCCAGCGTGTTGGCTGAGATCCAGGAGCACGTGTCAGCTTTCTGCTCTCATTGCTCCTGT
TCTGCATTGCCTCTTTCTGGGGTTTCCAAGAGGGGGGAGACTTTGCGCGGGGATGAGAT
AATGCCCCTTTTCTTAGGGTGGCTGCTGGGCAGCAGAGTGGCTCTGGGTCACTGTGGCAC
CAATGGGAGGCACCAGTGGGGGTGTGTTTGTGCAGGGGGGAAGCATTCACAGAATGGGG
CTGATCCTGAAGCTTGCAGTCCAAGGCTTTGTCTGTGTACCCAGTGAAATCCTTCCTCTG  6000
TTACATAAAGCCCAGATAGGACTCAGAAATGTAGTCATTCCAGCCCCCCTCTTCCTCAGA
TCTGGAGCAGCACTTGTTTGCAGCCAGTCCTCCCCAAAATGCACAGACCTCGCCGAGTGG
AGGGAGATGTAAACAGCGAAGGTTAATTACCTCCTTGTCAAAAACACTTTGTGGTCCATA
GATGTTTCTGTCAATCTTACAAAACAGAACCGAGAGGCAGCGAGCACTGAAGAGCGTGTT
CCCATGCTGAGTTAATGAGACTTGGCAGCTCGCTGTGCAGAGATGATCCCTGTGCTTCAT  6300
GGGAGGCTGTAACCTGTCTCCCATCGCCTTCACACCGCAGTGCTGTCCTGGACACCTCA
CCCTCCATAAGCTGTAGGATGCAGCTGCCCAGGGATCAAGAGACTTTTCCTAAGGCTCTT
AGGACTCATCTTTGCCGCTCAGTAGCGTGCAGCAATTACTCATCCCAACTATACTGAATG
GGTTTCTGCCAGCTCTGCTTGTTTGTCAATAAGCATTTCTTCATTTTGCCTCTAAGTTTC
TCTCAGCAGCACCGCTCTGGGTGACCTGAGTGGCCACCTGGAACCCGAGGGGCACAGCCA  6600
CCACCTCCCTGTTGCTGCTGCTCCAGGGACTCATGTGCTGCTGGATGGGGGGAAGCATGA
AGTTCCTCACCCAGACACCTGGGTTGCAATGGCTGCAGCGTGCTCTTCTTGGTATGCAGA
TTGTTTCCAGCCATTACTTGTAGAAATGTGCTGTGGAAGCCCTTTGTATCTCTTTCTGTG
GCCCTTCAGCAAAAGCTGTGGGAAAGCTCTGAGGCTGCTTTCTTGGGTCGTGGAGGAATT
GTATGTTCCTTCTTTAACAAAAATTATCCTTAGGAGAGAGCACTGTGCAAGCATTGTGCA  6900
CATAAAACAATTCAGGTTGAAAGGGCTCTCTGGAGGTTTCCAGCCTGACTACTGCTCGAA
GCAAGGCCAGGTTCAAAGATGGCTCAGGATGCTGTGTGCCTTCCTGATTATCTGTGCCAC
CAATGGAGGAGATTCACAGCCACTCTGCTTCCCGTGCCACTCATGGAGAGGAATATTCCC
TTATATTCAGATAGAATGTTATCCTTTAGCTCAGCCTTCCCTATAACCCCATGAGGGAGC
TGCAGATCCCCATACTCTCCCCTTCTCTGGGGTGAAGGCCGTGTCCCCAGCCCCCTTC  7200
CCACCCTGTGCCCTAAGCAGCCCGCTGGCCTCTGCTGGATGTGTGCCTATATGTCAATGC
CTGTCCTTGCAGTCCAGCCTGGGACATTTAATTCATCACCAGGGTAATGTGGAACTGTGT
CATCTTCCCCTGCAGGGTACAAAGTTCTGCACGGGGTCCTTTCGGTTCAGGAAAACCTTC
ACTGGTGCTACCTGAATCAAGCTCTATTTAATAAGTTCATAAGCACATGGATGTGTTTTC
CTAGAGATACGTTTTAATGGTATCAGTGATTTTTATTTGCTTGTTGCTTACTTCAAACA  7500
GTGCCTTTGGGCAGGAGGTGAGGGACGGGTCTGCCGTTGGCTCTGCAGTGATTTCTCCAG
GCGTGTGGCTCAGGTCAGATAGTGGTCACTCTGTGGCCAGAAGAAGGACAAAGATGGAAA
TTGCAGATTGAGTCACGTTAAGCAGGCATCTTGGAGTGATTTGAGGCAGTTTCATGAAAG
AGCTACGACCACTTATTGTTGTTTTCCCCTTTTACAACAGAAGTTTTCATCAAAATAACG
TGGCAAAGCCCAGGAATGTTTGGGAAAAGTGTAGTTAAATGTTTTGTAATTCATTTGTCG  7800
GAGTGCTACCAGCTAAGAAAAAGTCCTACCTTTGGTATGGTAGTCCTGCAGAGAATACA
ACATCAATATTAGTTTGGAAAAAAACACCACCACCACCAGAAACTGTAATGGAAAATGTA
AACCAAGAAATTCCTTGGGTAAGAGAGAAAGGATGTCGTATACTGGCCAAGTCCTGCCCA
GCTGTCAGCCTGCTGACCCTCTGCAGTTCAGGACCATGAAACGTGGCACTGTAAGACGTG
TCCCCTGCCTTTGCTTGCCCACAGATCTCTGCCCTTGTGCTGACTCCTGCACACAAGAGC  8100
ATTTCCCTGTAGCCAAACAGCGATTAGCCATAAGCTGCACCTGACTTTGAGGATTAAGAG
TTTGCAATTAAGTGGATTGCAGCAGGAGATCAGTGGCAGGGTTGCAGATGAAATCCTTTT
CTAGGGGTAGCTAAGGGCTGAGCAACCTGTCCTACAGCACAAGCCAAACCAGCCAAGGGT
TTTCCTGTGCTGTTCACAGAGGCAGGGCCAGCTGGAGCTGGAGGAGGTTGTGCTGGGACC
CTTCTCCCTGTGCTGAGAATGGAGTGATTTCTGGGTGCTGTTCCTGTGGCTTGCACTGAG  8400
CAGCTCAAGGGAGATCGGTGCTCCTCATGCAGTGCCAAAACTCGTGTTTGATGCAGAAAG
```

FIG. 4c

```
ATGGATGTGCACCTCCCTCCTGCTAATGCAGCCGTGAGCTTATGAAGGCAATGAGCCCTC
AGTGCAGCAGGAGCTGTAGTGCACTCCTGTAGGTGCTAGGGAAAATCTCTGGTTCCCAGG
GATGCATTCATAAGGGCAATATATCTTGAGGCTGCGCCAAATCTTTCTGAAATATTCATG
CGTGTTCCCTTAATTTATAGAAACAAACACAGCAGAATAATTATTCCAATGCCTCCCCTC  8700
GAAGGAAACCCATATTTCCATGTAGAAATGTAACCTATATACACACAGCCATGCTGCATC
CTTCAGAACGTGCCAGTGCTCATCTCCCATGGCAAAATACTACAGGTATTCTCACTATGT
TGGACCTGTGAAAGGAACCATGGTAAGAAACTTCGGTTAAAGGTATGGCTGCAAAACTAC
TCATACCAAAACAGCAGAGCTCCAGACCTCCTCTTAGGAAAGAGCCACTTGGAGAGGGAT
GGTGTGAAGGCTGGAGGTGAGAGACAGAGCCTGTCCCAGTTTTCCTGTCTCTATTTTCTG  9000
AAACGTTTGCAGGAGGAAAGGACAACTGTACTTTCAGGCATAGCTGGTGCCCTCACGTAA
ATAAGTTCCCCGAACTTCTGTGTCATTTGTTCTTAAGATGCTTTGGCAGAACACTTTGAG
TCAATTCGCTTAACTGTGACTAGGTCTGTAAATAAGTGCTCCCTGCTGATAAGGTTCAAG
TGACATTTTTAGTGGTATTTGACAGCATTTACCTTGCTTTCAAGTCTTCTACCAAGCTCT
TCTATACTTAAGCAGTGAAACCGCCAAGAAACCCTTCCTTTTATCAAGCTAGTGCTAAAT  9300
ACCATTAACTTCATAGGTTAGATACGGTGCTGCCAGCTTCACCTGGCAGTGGTTGGTCAG
TTCTGCTGGTGACAAAGCCTCCCTGGCCTGTGCTTTTACCTAGAGGTGAATATCCAAGAA
TGCAGAACTGCATGGAAAGCAGAGCTGCAGGCACGATGGTGCTGAGCCTTAGCTGCTTCC
TGCTGGGAGATGTGGATGCAGAGACGAATGAAGGACCTGTCCCTTACTCCCCTCAGCATT
CTGTGCTATTTAGGGTTCTACCAGAGTCCTTAAGAGGTTTTTTTTTTTTGGTCCAAAA  9600
GTCTGTTTGTTTGGTTTTGACCACTGAGAGCATGTGACACTTGTCTCAAGCTATTAACCA
AGTGTCCAGCCAAAATCAATTGCCTGGGAGACGCAGACCATTACCTGGAGGTCAGGACCT
CAATAAATATTACCAGCCTCATTGTGCCGCTGACAGATTCAGCTGGCTGCTCCGTGTTCC
AGTCCAACAGTTCGGACGCCACGTTTGTATATATTTGCAGGCAGCCTCGGGGGGACCATC

TCAGGAGCAGAGCACCGGCAGCCGCCTGCAGAGCCGGGCAGTACTCTCACCATGGCCATG  9900
               OVOMUCOID 5' UNTRANSLATED REGION
GCAGGTGTCTTCGTGCTGTTCTCTTTCGTGCTTTGTGGCTTCCTCCCAGGTGAGTAACTC
               OVOMUCOID 5' UNTRANSLATED REGION
CCAGAGTGCTGCAGAAGCTT                                          9920
```

FIG. 4d

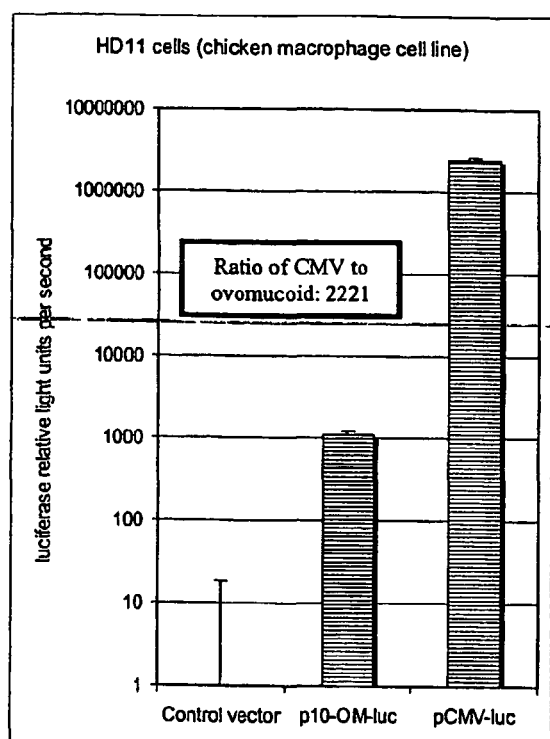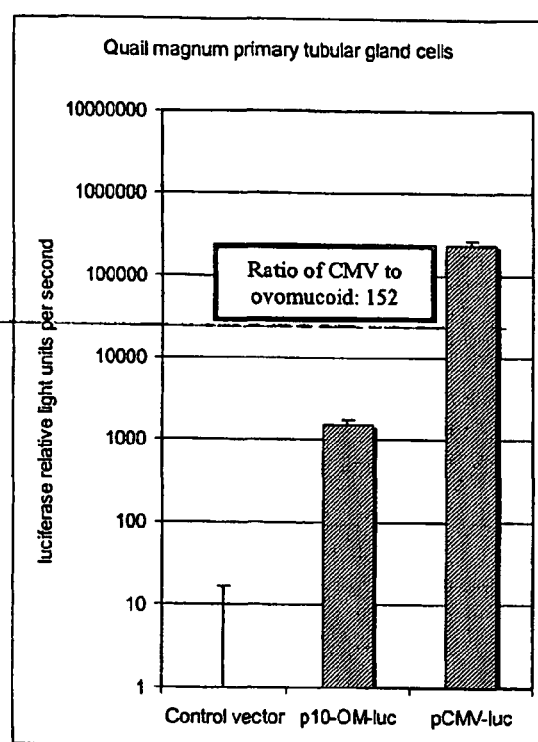
FIG. 6

TRANSGENIC AVIANS WITH AN OVOMUCOID GENE EXPRESSION CONTROL REGION LINKED TO A NUCLEOTIDE SEQUENCE ENCODING A HETEROLOGOUS POLYPEPTIDE

This application is a continuation-in-part of application Ser. No. 09/998,716 filed Nov. 30, 2001, now U.S. Pat. No. 6,875,588, which is hereby incorporated by reference in its entirety.

GOVERNMENT RIGHTS STATEMENT

This invention was made with government support under a grant from the National Institute of Standards and Technology. Therefore, the U.S. Government may have certain rights in this invention.

1. FIELD OF THE INVENTION

The present invention relates generally to the identification of an avian ovomucoid gene expression control region, particularly from the chicken. More specifically, the invention relates to recombinant nucleic acids and expression vectors, transfected cells and transgenic animals, especially chickens, that comprise the avian ovomucoid gene expression control region operably linked to a heterologous polypeptide-encoding nucleic acid.

2. BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins or other substances of pharmaceutical interest (Gordon et al., Biotechnology 5: 1183-1187 (1987); Wilmut et al., Theriogenology 33: 113-123 (1990)) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (See e.g., Krimpenfort et al., in U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infindibulum of the oviduct where it is fertilized, if sperm are present, and then moves into the magnum of the oviduct which is lined with tubular gland cells. These cells secrete the egg-white proteins, including ovalbumin, ovomucoid, ovoinhibitor, conalbumin, ovomucin and lysozyme, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. As a result, efforts have been made to create transgenic chickens expressing heterologous proteins in the oviduct.

Chicken oviduct cells, when stimulated by steroid hormones during egg-laying, secrete three principal polypeptides, ovalbumin, ovomucoid and lysozyme (Tsai et al., Biochemistry 17: 5773-5779 (1978)). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells. (Hynes et al., Cell 11:923-932 (1977)).

Detailed restriction enzyme analysis of fragments of chicken genomic DNA have shown that the ovomucoid-encoding sequence includes seven intronic sequences (Lindenmaier et al., Nuc. Acid Res. 7;1221-1232 (1979); Catterall et al., Nature 278: 323-327 (1979); Lai et al., Cell 18:829-842 (1979)). Short stretches of the 5' flanking region of the ovomucoid gene have been sequenced (Lai et al., Cell 18: 829-842 (1979); Genbank Accession No. J00897), but extending only 579 bases upstream of the recognized transcription start site. The 5' flanking region of the ovomucoid gene has been isolated (Catterall et al., Nature 278: 323-327 (1979); Lai et al., Cell 18: 829-842 (1979)), but not generally characterized beyond low-resolution restriction site mapping. Scott et al. in Biochemistry 26: 6831-6840 (1987) identified a CR1-like region within the 10 kb chicken genomic DNA located between the ovoinhibitor-encoding region and the downstream ovomucoid gene. The ovoinhibitor-encoding cDNA and the attached 3'-untranslated region, which extends into the 10 kb ovoinhibitor-ovomucoid region, were also sequenced (Scott et al. J. Biol. Chem. 262: 5899-5907 (1987)).

The chicken ovomucoid gene, therefore, is highly expressed in the tubular glands of the mature hen oviduct and represents a suitable candidate for an efficient promoter for heterologous protein production in transgenic animals, especially animals. The regulatory region of the ovomucoid locus extends over a nucleic acid region of about 10 kb of DNA 5' upstream of the transcription start site, and comprises at least one recognized element, the CR1.

3. SUMMARY OF THE INVENTION

The present invention relates to nucleic acids comprising an avian ovomucoid gene expression control region, which is useful for the expression of nucleotide sequences encoding a polypeptide of interest in a transfected avian cell such as, for example, an oviduct cell. In a preferred embodiment the polypeptide is heterologous, i.e., not the ovomucoid protein product, and more preferably, is a mammalian, most preferably, a human polypeptide.

One aspect of the present invention provides a nucleic acid isolated from a region immediately 5' upstream of a transcription start site of the chicken (or other avian) ovomucoid gene locus. The nucleic acid comprises an avian nucleic acid sequence comprising an ovomucoid gene expression control region comprising at least one avian CR1 repeat element, and a proximal ovomucoid promoter. Interspersed between these constituent elements may be stretches of nucleic acid that may serve at least to organize the gene regulatory elements in an ordered array relative to a polypeptide-encoding region. In one embodiment of the present invention the ovomucoid gene expression control region is isolated from a chicken. In a specific embodiment, the ovomucoid gene expression control region has a nucleotide sequence of SEQ ID NO:26. In other embodiments, the ovomucoid gene expression control region is at least 75%, at least 95%, or at least 99% identical to SEQ ID NO:26 and directs expression of a polypeptide encoding nucleotide sequence in an avian oviduct cell.

The avian ovomucoid gene expression control region of the present invention is useful for directing tissue-specific expression of a polypeptide-encoding nucleic acid. The avian ovomucoid gene expression control region may be operably linked with a selected nucleic acid insert, wherein the nucleic acid insert encodes a polypeptide, preferably heterologous, desired to be expressed in a transfected cell. The nucleic acid insert may be placed in frame with a nucleotide sequence encoding a signal peptide. Translation initiation may start with the signal peptide and continue through the nucleic acid insert, thereby producing an expressed polypeptide having the desired amino acid sequence.

The recombinant DNA of the present invention may further comprise a polyadenylation signal sequence that will allow the transcript directed by the ovomucoid gene expression control region of the invention to proceed beyond the nucleic acid insert encoding a heterologous polypeptide (i.e., not the ovomucoid protein that is expressed from the endogenous gene containing the ovomucoid gene expression control region) and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like. Optionally, the nucleic acid of the invention may also comprise gene expression control elements, e.g. promoters, enhancers, IRES's, from other than an ovomucoid gene and may even be from a non-avian gene.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, ovomucoid, ovomucin and ovotransferrin of chicken.

Yet another aspect of the present invention is expression vectors suitable for delivery to a recipient cell for expression of heterologous protein coding sequences in the vector therein. The expression vector of the present invention may comprise an avian ovomucoid gene expression control region operably linked to a nucleic acid insert encoding a non-ovomucoid polypeptide, and optionally, a polyadenylation signal sequence. The expression vector may further comprise a bacterial plasmid sequence, a viral nucleic acid sequence, or fragments or variants thereof that may allow for replication of the vector in a suitable host. As also contemplated in the present invention the nucleic acid is a YAC, BAC, bacteriophage-derived artificial chromosome (BBPAC), cosmid or P1 derived artificial chromosome (PAC).

The present invention further relates to nucleic acid vectors and transgenes inserted therein that incorporate multiple polypeptide-encoding regions, wherein a first polypeptide-encoding region is operatively linked to a transcription promoter and a second polypeptide-encoding region is operatively linked to an Internal Ribosome Entry Sequence (IRES). For example, the vector may contain coding sequences for two different heterologous proteins (e.g., the heavy and light chains of an immunoglobulin).

Such nucleic acid constructs, when inserted into the genome of a bird and expressed therein, will generate individual polypeptides that may be post-translationally modified, for example, glycosylated or, in certain embodiments, be present as complexes, such as heterodimers with each other.

Another aspect of the present invention is a method of expressing a heterologous polypeptide in a eukaryotic cell by transfecting the cell with a recombinant DNA comprising an avian ovomucoid gene expression control region operably linked to a nucleic acid insert encoding the heterologous polypeptide and, optionally, a polyadenylation signal sequence, and culturing the transfected cell in a medium suitable for expression of the heterologous polypeptide under the control of the avian ovomucoid gene expression control region. In preferred embodiments the polypeptide is a cytokine, growth factor, enzyme, structural protein, and more preferably, an immunoglobulin, or subunit thereof. Other preferred embodiments the polypeptide is a mammalian, preferably a human polypeptide or derived from a human or mammalian polypeptide.

Also within the scope of the present invention are recombinant cells, tissues and animals, in particular avians and avian eggs, most preferably chicken, containing recombinant nucleic acid molecules according to the present invention and described above. In preferred embodiments, the level of expression of the heterologous protein is greater than 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams in an egg (preferably the egg white) produced by the transgenic avian of the invention. In one embodiment of the present invention, the transformed cell is a chicken oviduct cell and the nucleic acid comprises the chicken ovomucoid gene expression control region, a nucleic acid insert encoding a heterologous polypeptide of interest, e.g. human interferon α2, which optionally is codon optimized for expression in an avian cell, and an SV40 polyadenylation sequence.

3.1 Definitions

The term "animal" is used herein to include all vertebrate animals, including humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, e.g, plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid that has been removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The "isolated nucleic acid" does not include nucleic acids that are members of a library, e.g. cDNA or genomic library, unless identified and separated from the other members of the library. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

It is advantageous for some purposes that a nucleotide sequence is in purified form. The term "purified" in reference to nucleic acid represents that the sequence has increased purity relative to the natural environment, preferably, 50%, 60%, 70%, 80%, 90%, 95%, or 99% pure.

The terms "polynucleotide" and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling ligands.

The term "fragment" as used herein to refers to an at least 10, 20, 50, 75, 100, 150, 200, 250, 300, 500, 1000, 2000 or 5000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to an at least 5, 10, 20, 30, 40, 50, 75, 100, 150, 200, 250, 300, 400, 500, 1000, 2000, or 5000 amino acid portion of a polypeptide, which portion is cleaved from a naturally occurring polypeptide by proteolytic cleavage by at least one protease, or is a portion of the naturally occurring polypeptide synthesized by chemical methods or using recombinant DNA technology (e.g., expressed from a portion of the nucleotide sequence encoding the naturally occurring polypeptide) known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The terms "operably linked" or "operatively linked" refer to the configuration of the coding and control sequences so as to perform the desired function. Thus, control sequences operably linked to a coding sequence are capable of effecting the expression of the coding sequence and regulating in which tissues, at what developmental timepoints, or in response to which signals, etc., a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences, can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a nucleic acid vector to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter' as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al., 2000, *Development* 127: 1953-1960; Gemer et al., 2000, *Int. J. Hyperthermia* 16: 171-81; Rang and Will, 2000, *Nucleic Acids Res*. 28: 1120-5; Hagihara et al., 1999, *Cell Transplant* 8: 4314; Huang et al., 1999, *Mol. Med*. 5: 129-37; Forster et al., 1999, *Nucleic Acids Res*. 27: 708-10; Liu et al., 1998, *Biotechniques* 24: 624-8, 630-2; the contents of which have been incorporated herein by reference in their entireties).

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a ovomucoid gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of *Karlin & Attschul* (1990) Proc. Natl. Acad. Sci. 87: 2264-2268, modified as in *Karlin & Attschul* (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the ovomucoid gene expression control region operably linked to a nucleotide sequence coding at least one polypeptide. As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to, e.g., the male germ cells using specific ligands that are recognized by receptors on the cell surface of the germ cell, such as the c-kit ligand or modifications thereof.

Other preferred transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian or avian cell (including within a transgenic mammal or avian) or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

Pharmaceutical compositions comprising agents that will modulate the regulation of the expression of a polypeptide-encoding nucleic acid operably linked to a ovomucoid gene expression control region can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as *Remmington's Pharmaceutical Science*, 17th edition, 1985 may be consulted to prepare suitable preparations, without undue experimentation. Dosages can generally range from a few hundred milligrams to a few grams.

As used herein, a "transgenic animal" is any non-human animal, such as an avian species, including the chicken, in which one or more of the cells of the animal contain a heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g. either agonistic or antagonistic forms, or in which the gene has been disrupted. In certain embodiments, the genome of the animal has been modified such that a heterologous gene expression element is inserted so as to be operably linked to an endogenous coding sequence. The terms "chimeric animal" or "mosaic animal" are used herein to refer to animals in which the recombinant gene is found, or in which the recombinant gene is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A trangene also includes a regulatory sequence designed to be inserted into the genome such that it regulates the expression of an endogenous coding sequence, e.g., to increase expression and or to change the timing and or tissue specificity of expression, etc. (e.g., to effect "gene activation").

The term "cytokine" as used herein refers to any secreted polypeptide that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "antibody" as used herein refers to polyclonal and monoclonic antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, e.g., as produced by a Fab expression library, anti-idiotypic (anti-Id) antibodies, intrabodies, synthetic antibodies, and epitope-binding fragments of any of the above.

The term "immunoglobulin polypeptide" as used herein refers to a polypeptide derived from a constituent polypeptide of an immunoglobulin. An "immunoglobulin polypeptide" may be, but is not limited to, an immunoglobulin (preferably an antibody) heavy or light chain and may include a variable region, a diversity region, joining region and a constant region or any combination, variant or truncated form thereof. The term "immunoglobulin polypeptides" further includes single-chain antibodies comprised of, but not limited to, an immunoglobulin heavy chain variable region, an immunoglobulin light chain variable region and optionally a peptide linker.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

This description uses gene nomenclature accepted by the Cucurbit Genetics Cooperative as it appears in the *Cucurbit Genetics Cooperative Report* 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

Abbreviations

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide.

Additional objects and aspects of the present invention will become more apparent upon review of the detailed description set forth below when taken in conjunction with the accompanying figures, which are briefly described as follows.

4. BRIEF DESCRIPTION OF THE FIGURES

FIG. 3 shows the PCR primers SEQ ID NOS: 1-25 used to PCR amplify and/or sequence the approximately 10 kb nucleic acid region that is 5' upstream of the chicken ovomucoid transcription start site.

FIG. 4a-d shows the nucleic acid sequence SEQ ID NO: 26 of the approximately 10 kb nucleic acid region that is 5' upstream of the chicken ovomucoid transcription start site.

Figure 5:
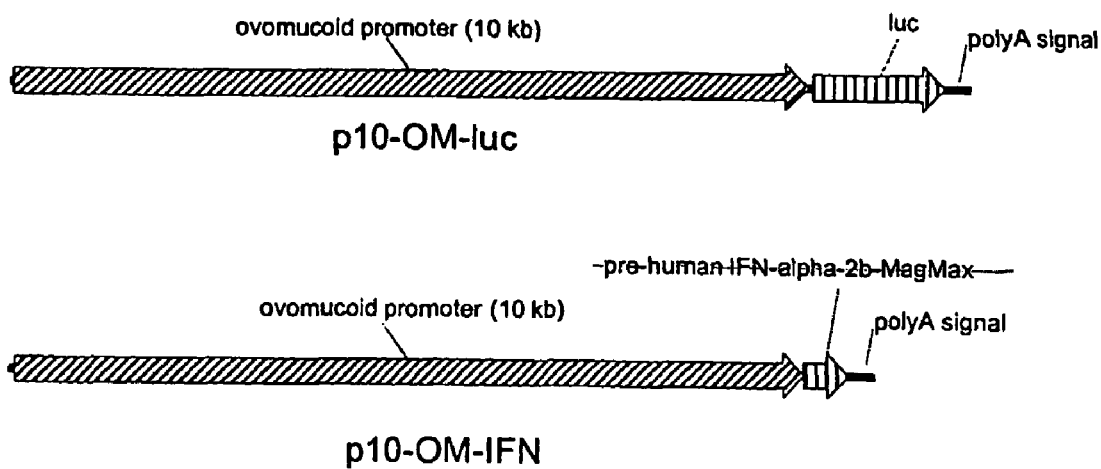

FIG. 5 illustrates the 10 kb ovomucoid promoter linked to the luciferase or human IFNα-2b coding sequences.

FIG. 6A shows the results of transfections of plasmids containing the ovomucoid promoter or CMV promoter linked to a luciferase gene into HD11 cells, a chicken myeloid cell line.

FIG. 6B shows the results of transfections of plasmids containing the ovomucoid promoter or CMV promoter linked to a luciferase gene into primary quail tubular gland cells isolated from the magnum portion of the oviduct of a laying quail hen.

Figure 7:
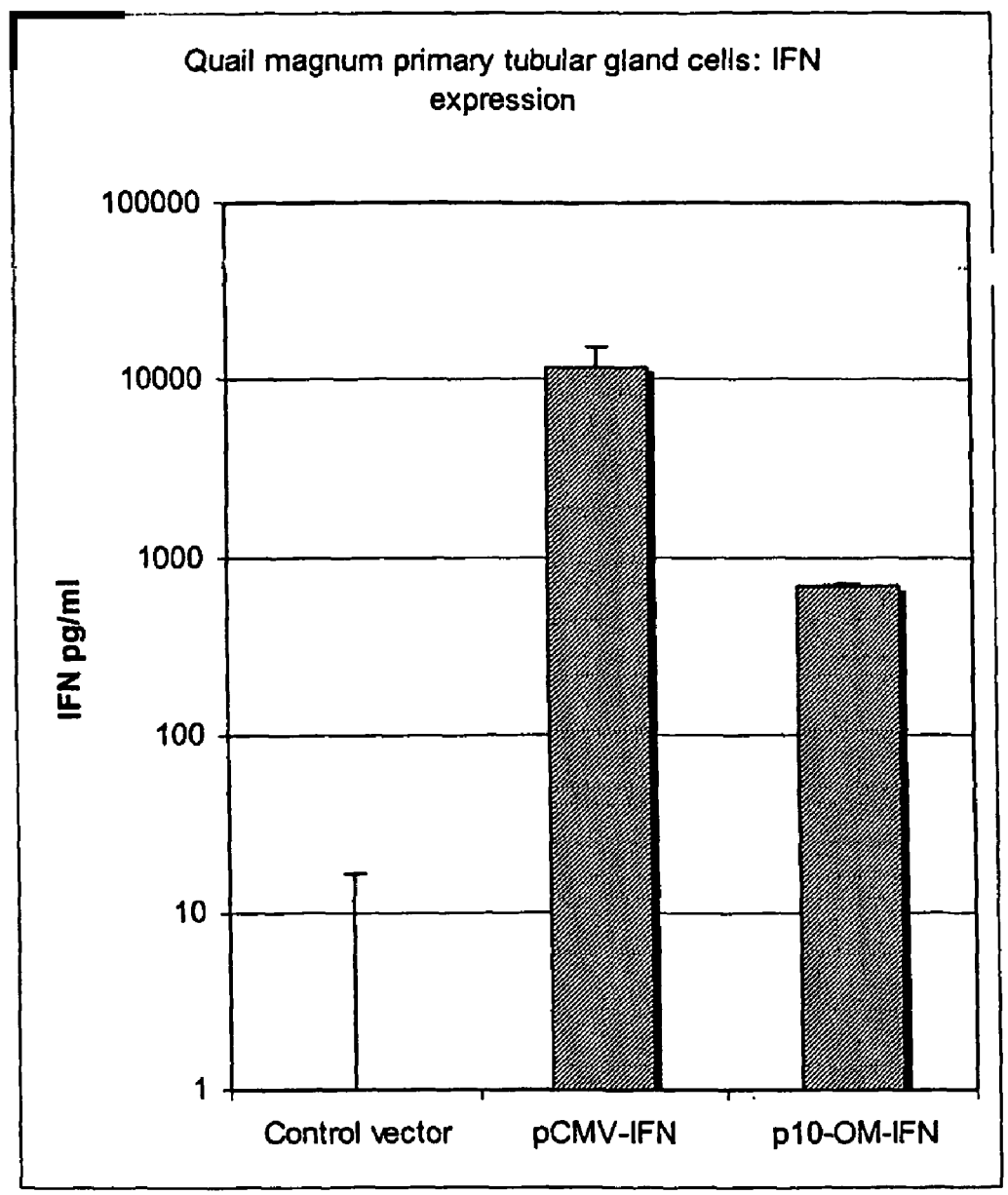

FIG. 7 shows the results of transfections of plasmids containing the ovomucoid promoter or CMV promoter linked to a interferon gene into primary quail tubular gland cells isolated from the magnum portion of the oviduct of a laying quail hen.

5. DETAILED DESCRIPTION OF THE INVENTION 5.1 Chicken Ovomucoid Gene Expression Control Region Nucleic Acid Sequences A series of PCR amplifications of template chicken genomic DNA were used to isolate the gene expression control region of the chicken ovomucoid locus. The region of the chicken genome lying between the 3' end of the ovoinhibitor gene and the 5' transcription start site of the ovomucoid gene was PCR amplified using the primers OVINs 2, 5'-TAGGCAGAGCAATAGGACTCTCAAC-CTCGT-3' (SEQ ID NO: 1) and OVMUa2, 5'-AAGCTTCT-GCAGCACTCTGGGAGTTACTCA-3' (SEQ ID NO: 2) as described in detail in Example 1 below and FIG. 1. The approximately 10 kb fragment was blunt-ended and cleaved with the restriction endonuclease Bam HI. The resulting fragments of about 4.7 kb and 5.5 kb were subcloned into the linearized plasmid vector pBluescript KS II (+/−) (Stratagene, La Jolla, Calif.). Each insert was sequenced using the primers SEQ ID NOS: 5-25 shown in FIGS. 2 and 3 and as described in Example 3 below. The compiled nucleic acid sequence (SEQ ID NO: 26) of the approximately 10 kb nucleic acid region that is 5' upstream of the chicken ovomucoid transcription start site is shown in FIG. 4.

SEQ ID NO: 26 includes the ovoinhibitor gene 3' untranslated region described by Scott et al. (J. Biol. Chem. 262: 5899-5909 (1987)) from bases positions 1-255 as shown in FIG. 4. A CR1-like element (Scott et al., Biochemistry 26: 6831-6840 (1987); Genbank Accession No: M17966) is located at base positions 2761-3024 as shown in FIG. 4. The region of SEQ ID NO: 26 from base positions 9403-9920, as shown in FIG. 4, has been described in Genbank Accession No: J00897 and in Lai et al., Cell 18: 829-842 (1979) and includes a portion of the 5' untranslated region of the ovomucoid gene.

It is contemplated that any nucleic acid sequence encoding a polypeptide may be operably linked to the avian ovomucoid gene expression control region of the invention so as to be expressed in a transfected avian cell. For example, a plasmid construct contacting the cloned ovomucoid promoter region and a desired polypeptide-encoding nucleic acid sequence may be transfected into cultured quail or chicken oviduct cells, which may then be incubated to synthesize a polypeptide detectable with antibodies directed against the desired polypeptide.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin Immunoglobulins and genetically engineered antibodies, including immunotoxins that bind to surface antigens on human tumor cells and destroy them, can also be expressed for use as pharmaceuticals or diagnostics. It is contemplated that immunoglobulin polypeptides expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

The chicken ovomucoid gene expression control region of the present invention comprises the nucleotide elements that are positioned 5' upstream of the transcription start site of the native chicken ovomucoid locus and which are necessary for the regulated expression of a downstream polypeptide-encoding nucleic acid. It is contemplated that this region includes those transcription control regions regulatable by hormones including, for example, steroid hormones and the like.

One aspect of the present invention, therefore, provides a novel isolated nucleic acid that comprises the nucleotide sequence SEQ ID NO: 26, shown in FIG. 4, (Genbank Accession No: AF 453747) and derivatives and variants thereof, that is located immediately 5' upstream of the transcription start site of the chicken ovomucoid gene locus.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 26, as shown in FIG. 4, or a variant thereof. SEQ ID NO: 26 was cloned into pBluescript KSII (+/−) vector, as described in Example 2, and named pBS-OVMUP-10. pBS-OVMUP-10 was deposited with American Type Culture Collection (ATCC) as ATCC No. PTA-4821, on Nov. 26, 2002 under the conditions set forth in the Budapest Treaty.

Fragments of a nucleic acid comprising a portion of the subject ovomucoid gene expression control region are also within the scope of the invention. As used herein, a fragment of the nucleic acid comprising an active portion of a ovomucoid gene expression control region refers to a nucleotide sequence having fewer nucleotides than the nucleotide sequence comprising the entire nucleic acid sequence of the ovomucoid gene expression control region.

A fragment of the ovomucoid gene expression control region may contain one or more of the following elements: the ovoinhibitor gene 3' untranslated region from bases positions 1-255 as shown in FIG. 4, a CR1-like element located at base positions 2761-3024 as shown in FIG. 4, the region from base positions 9403-9920, as shown in FIG. 4 which includes a portion of the 5' untranslated region of the ovomucoid gene. Alternatively, the fragment may be 10, 20, 50, 75, 100, 150, 200, 250, 300, 500, 1000, 2000, 4000, 5000, 6000, 7000, 8000 or 9000 nucleotides in length and be capable of directing expression of an operably linked heterologous gene sequence, particularly in an avian oviduct cell.

In one embodiment of the present invention, the nucleotide sequence of the isolated DNA molecule of the present invention may be used as a probe in nucleic acid hybridization assays for the detection of the ovomucoid gene expression control region. The nucleotide sequence of the present invention may be used in any nucleic acid hybridization assay system known in the art, including, but not limited to, Southern blots (Southern, E. M. J. Mol. Biol. 98: 508 (1975)), Northern blots (Thomas et al., Proc. Natl. Acad. Sci. 77: 5201-05 (1980)), and Colony blots (Grunstein et al., Proc. Natl. Acad. Sci. 72: 3961-65 (1975)), which are hereby incorporated by reference in their entireties. Alternatively, the isolated DNA molecules of the present invention can be used in a gene amplification detection procedure such as a polymerase chain reaction (Erlich et al., Science 252: 1643-51 (1991), which is hereby incorporated by reference in its entirety) or in restriction fragment length polymorphism (RFLP) diagnostic techniques, as described in Watson et al., (2d ed. 1992), Recombinant DNA, Scientific American Books, 519-522, 545-547, which is hereby incorporated by reference.

Nucleic acids constructed in accordance with the present invention can be labeled to provide a signal as a means of detection. For example, radioactive elements such as $^{32}$P, $^{3}$H, and $^{35}$S or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide*, 2nd Edition, 1991 (Promega Corp., Madison, Wis., the content of which is incorporated herein in its entirety) may be consulted to select an appropriate labeling protocol without undue experimentation.

In another embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived ovomucoid gene expression control region-comprising nucleic acid molecule as depicted in SEQ ID NO: 26 and directs expression of a polypeptide encoding sequence in an avian oviduct cell, when operably linked to the polypeptide encoding sequence.

In another embodiment of the present invention, an isolated nucleic acid molecule of the present invention includes a nucleic acid that hybridizes to SEQ ID NO: 26 or the reverse complement thereof, or the insert in pBS-OVMUP-10, under high, moderate or low stringency hybridization conditions.

In another embodiment of the present invention, an avian ovomucoid gene expression control region gene or nucleic acid molecule can be an allelic variant of SEQ ID NO: 26 or a homolog from a different avian, e.g., quail, duck, etc.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized oligonucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken ovomucoid gene expression control region nucleic acid molecule (SEQ ID NO: 26) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain ovomucoid gene expression control region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian ovomucoid gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken ovomucoid gene expression control region include, but are not limited to, GenBank and the mammalian Gene Index database of The Institute of Genomics Research (TIGR).

Codon-Optimized Proteins

Another aspect of the present invention is a recombinant DNA molecule comprising the novel isolated avian ovomucoid gene expression control region of the present invention operably linked to a selected polypeptide-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed polypeptide having the desired amino acid sequence.

It is anticipated that the recombinant DNA may further comprise a polyadenylation signal sequence that will allow the transcript directed by the novel ovomucoid gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof.

Another aspect of the present invention is to provide nucleic acid sequences of a protein optimized for expression in avian cells, and derivatives and fragments thereof.

One embodiment of the present invention is a recombinant DNA molecule comprising the isolated avian ovomucoid gene expression control region of the present invention, operably linked to a nucleic acid insert encoding a polypeptide, and a polyadenylation signal sequence optionally operably linked thereto. It is contemplated that when the recombinant DNA is to be delivered to a recipient cell for expression therein, the sequence of the nucleic acid sequence may be modified so that the codons are optimized for the codon usage of the recipient species. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon α2b polypeptide optimized for codon-usage by the chicken is used. Optimization of the sequence for codon usage is useful in elevating the level of translation in avian eggs.

It is contemplated to be within the scope of the present invention for any nucleic acid encoding a polypeptide to be optimized for expression in avian cells. It is further contemplated that the codon usage may be optimized for a particular avian species used as a source of the host cells. In one embodiment of the present invention, the heterologous polypeptide is encoded using the codon-usage of a chicken.

In yet another embodiment of the present invention, the recombinant DNA comprises the isolated avian ovomucoid gene expression control region operably linked to a nucleic acid encoding a human interferon α2b and the SV40 polyadenylation sequence.

The protein of the present invention may be produced in purified form by any known conventional technique. In a preferred embodiment, the protein is purified from chicken eggs, preferably egg whites. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Multimeric Proteins

The invention, in preferred embodiments, provides methods for producing multimeric proteins, preferably immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 2001, by Rapp, published as US-2002-0108132-A1 on Aug. 8, 2002, and U.S. patent application Ser. No. 10/251,364, filed Sep. 18, 2002, by Rapp, both of which are incorporated herein by reference in their entirety. In one embodiment of the present invention, therefore, the multimeric protein is an immunoglobulin wherein the first and second heterologous polypeptides are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by the transcriptional unit of an expression vector may also be an immunoglobulin light chain polypeptide comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In preferred embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen comprising the step of producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In an embodiment of this method of the present invention, the isolated heterologous protein is an antibody capable of selectively binding to an antigen. In one embodiment, the antibody may be generated by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin polypeptide. The method may further comprise the step of combining a plurality of isolated heterologous immunoglobulin polypeptides, thereby producing an antibody capable of selectively binding to an antigen. In this embodiment, two individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides may be isolated from their respective sera and eggs and combined in vitro to generate a binding site capable of binding an antigen.

Examples of therapeutic antibodies that can be used in methods of the invention include but are not limited to HERCEPTIN® (Trastuzumab) (Genentech, Calif.) which is a humanized anti-HER2 monoclonal antibody for the treatment of patients with metastatic breast cancer; REOPRO®

(abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primated anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

Recombinant Nucleic Acids, and Expression thereof, under the Control of an Avian Ovomucoid Promoter Another potentially useful application of the novel isolated ovomucoid gene expression control region of the present invention is the possibility of increasing the amount of a heterologous protein present in a bird, (especially the chicken) by gene transfer. In most instances, a heterologous polypeptide-encoding nucleic acid insert transferred into the recipient animal host will be operably linked with the ovomucoid gene expression control region to allow the cell to initiate and continue production of the genetic product protein. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the polypeptide-encoding nucleic acid insert of the recombinant DNA molecule is heterologous (i.e. not normally present). Alternatively, as described more fully below, the recombinant DNA molecule may be introduced into cells which normally contain the polypeptide-encoding nucleic acid insert of the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated ovomucoid gene expression control region.

U.S. Pat. No. 4,237,224 to Cohen & Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for replication OR expression of a polypeptide-encoding nucleic acid of the vector therein. It is contemplated to be within the scope of the present invention for the expression vector to comprise an isolated avian ovomucoid gene expression control region operably linked to a nucleic acid insert encoding a polypeptide, and optionally a polyadenylation signal sequence. The expression vector of the present invention may further comprise a bacterial plasmid sequence, a viral nucleic acid sequence, or fragments or variants thereof that may allow for replication of the vector in a suitable host.

The novel isolated avian ovomucoid gene expression control region of the present invention (SEQ ID NO: 26) and a polypeptide-encoding nucleic acid sequence operably linked thereto and optionally a polyadenylation signal sequence may be introduced into viruses such as vaccinia virus. Methods for making a viral recombinant vector useful for expressing a protein under the control of the ovomucoid promoter are analogous to the methods disclosed in U.S. Pat. Nos. 4,603,112; 4,769,330; 5,174,993; 5,505,941; 5,338,683; 5,494,807; 4,722,848; Paoletti, E. Proc. Natl. Acad. Sci. 93: 11349-11353 (1996); Moss Proc. Natl. Acad. Sci. 93: 11341-11348 (1996); Roizman Proc. Natl. Acad. Sci. 93: 11307-11302 (1996); Frolov et al. Proc. Natl. Acad. Sci. 93: 11371-11377 (1996); Grunhaus et al. Seminars in Virology 3: 237-252 (1993) and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier, F. W. et. al. (1990) "Use of T7 RNA Polymerase to Direct Expression of Cloned Genes" Gene Expression Technology, vol. 185, which is hereby incorporated by reference in its entirety) and any derivatives thereof, cosmid vectors and, in preferred embodiments, artificial chromosomes, such as, but not limited to, YACs, BACs, BBPACs or PACs. Such artificial chromosomes are useful in that a large nucleic acid insert can be propagated and introduced into the avian cell. Recombinant molecules can be introduced into cells via transformation, particularly transduction, conjugation, mobilization, or electroporation. The DNA sequences are cloned into the vector using standard cloning procedures in the art, as described by Sambrook et al. Molecular Cloning: A Laboratory Manual, 3$^{rd}$ ed., Cold Spring Harbor Laboratory, Cold Springs Harbor, N.Y. (2001), which is hereby incorporated by reference in its entirety.

The vectors of the invention comprise one or more nucleotide sequences encoding a heterologous protein desired to be expressed in the transgenic avian, as well as regulatory elements such as promoters, enhancers, Matrix Attachment Regions, IRES's and other translation control elements, transcriptional termination elements, polyadenylation sequences, etc. In particular embodiments, the vector of the invention contains at least two nucleotide sequences coding for heterologous proteins, for example, but not limited to, the heavy and light chains of an immunoglobulin.

The present invention further relates to nucleic acid vectors and transgenes inserted therein, having the avian ovomucoid gene expression control region of the invention, that incorporate multiple polypeptide-encoding regions, wherein a first polypeptide-encoding region is operatively linked to a transcription promoter and a second polypeptide-encoding region is operatively linked to an IRES. For example, the vector may contain coding sequences for two different heterologous proteins (e.g., the heavy and light chains of an immunoglobulin).

Such nucleic acid constructs, when inserted into the genome of a bird and expressed therein, will generate individual polypeptides that may be post-translationally modified, for example, glycosylated or, in certain embodiments, form complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to the ovomucoid gene expression control region of the invention are introduced into the avian cell. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Once the ovomucoid gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian or avian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection, cytoplasmic injection, pronuclear injection and the like.

Another aspect of the present invention, therefore, is a method of expressing a heterologous polypeptide in a eukaryotic cell by transfecting the cell with a recombinant DNA comprising an avian ovomucoid gene expression control region operably linked to a nucleic acid insert encoding a polypeptide and, optionally, a polyadenylation signal sequence, and culturing the transfected cell in a medium suitable for expression of the heterologous polypeptide under the control of the avian ovomucoid gene expression control region.

In preferred embodiments, the ovomucoid gene expression control region directs a level of expression of the heterologous protein in avian eggs that is greater than 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams per egg. Such levels of expression can be obtained using the expression control regions of the invention.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken ovomucoid gene expression control region, a nucleic acid insert encoding a human interferon α2d with codons optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian ovomucoid gene expression control region according to the present invention is produced in the white of an egg.

Viral Vector Cell Transformation

An exemplary approach for the in vivo introduction of a polypeptide-encoding nucleic acid operably linked to the subject novel isolated ovomucoid gene expression control region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid comprising a ovomucoid gene expression control region, thereby rendering the retrovirus replication defective. Protocols for producing recombinant retroviruses and for infecting cells in vitro or in vivo with such viruses can be found in Current Protocols in Molecular Biology, Ausubel et al. (1989) (eds.) Greene Publishing Associates, Sections 9.10-9.14 and other standard laboratory manuals. Examples of suitable retroviruses include pLJ, pZIP, pWE and pEM which are all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., Proc. Natl. Acad. Sci. 86: 9079-9083 (1989); Julan et al., J. Gen. Virol. 73: 3251-3255 (1992); and Goud et al., Virology 163: 251-254 (1983)) or coupling cell surface ligands to the viral env proteins (Neda et al., J. Biol. Chem. 266: 14143-14146 (1991)), all of which are incorporated herein by reference in their entireties. Coupling can be in the form of the chemical cross-linking with a protein or other moiety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., BioTechniques 6: 616 (1988); Rosenfeld et al., Science 252: 43 1434 (1991); and Rosenfeld et al., Cell 68: 143-155 (1992)), all of which are incorporated herein by reference in their entireties. Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., Cell 16:683 (1979); Berkner et al., supra; and Graham et al., in Methods in Molecular Biology, E. J. Murray, (1991) Ed. (Humana, Clifton, N.J.) vol. 7. pp. 109-127), all of which are incorporated herein by reference in their entireties. Expression of an inserted gene such as, for example, encoding the human interferon α2b, can be under control of the exogenously added ovomucoid gene expression control region sequences.

Yet another viral vector system useful for delivery of, for example, the subject avian ovomucoid gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268: 3781-3790 (1993)), all of which are incorporated herein by reference in their entireties.

Non-viral Expression Vectors

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject ovomucoid gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated ovomucoid gene expression control region of the present invention can be entrapped in liposomes bearing positive charges on their surface (e.g., lipofectins) and (optionally) which are tagged with antibodies against cell surface antigens of the target tissue (Mizuno et al., NO Shinkei Geka 20:547-551 (1992); PCT publication W091/06309; Japanese patent application 1047381; and European patent publication EP-A-43075), all of which are incorporated herein by reference in their entireties.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), all of which are incorporated herein by reference in their entireties. It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., Science 260: 926 (1993); Wagner et al., Proc. Natl. Acad. Sci. 89:7934 (1992); and Christiano et al., Proc. Natl. Acad. Sci. 90:2122 (1993)), all of which are incorporated herein by reference in their entireties. It is further contemplated that a recombinant DNA molecule comprising the novel isolated ovomucoid gene expression control region of the present invention may be delivered to a recipient host cell by other non-viral methods including by gene gun, microinjection, sperm-mediated transfer as described in PCT/US02/30156, filed Sep. 23, 2002 and incorporated herein by reference in its entirety, nuclear transfer, or the like.

Transgenic Animals

Another aspect of the present invention concerns transgenic animals, such as chickens that contain a transgene comprising the novel isolated ovomucoid gene expression control region of the present invention and which preferably (though optionally) express a heterologous gene in one or more cells in the animal. Suitable methods for the generation of transgenic avians having heterologous DNA incorporated therein, for example, cytoplasmic injection and pronuclear injection, are described, for example, in U.S. patent application Ser. No: 10/251,364, entitled "Methods of Generating Transgenic Avians Using Microinjection into the Cytoplasm of an Avian Egg or Embryo", by Rapp et al., filed Sep. 18, 2002, and incorporated herein by reference in its entirety.

In various embodiments of the present invention, the expression of the transgene may be restricted to specific subsets of cells, tissues or developmental stages utilizing, for example, cis-acting sequences acting on the ovomucoid gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous polypeptide and operably linked to the novel isolated avian ovomucoid gene expression control region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian ovomucoid gene expression control region comprising the nucleic acid sequence in SEQ ID NO: 26, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding a polypeptide has a codon complement optimized for protein expression in an avian.

In another embodiment of the transgenic avian of the present invention, the transgenic avian produces the heterologous polypeptide in the serum or an egg white. In another embodiment of the transgenic avian of the present invention, the transgenic avian produces the heterologous polypeptide in an egg white.

The present invention is further illustrated by the following examples, which are provided by way of illustration and should not be construed as limiting. The contents of all references, published patents and patents cited throughout the present application are hereby incorporated by reference in their entireties.

EXAMPLE 1

PCR Amplification of Ovomucoid Promoter

Sense primer OVINs2, 5'-TAGGCAGAGCAATAG-GACTCTCAACCTCGT-3' (SEQ ID NO: 1) and the antisense primer, OVMUa2, 5'-AAGCTTCTGCAG-CACTCTGGGAGTTACTCA-3' (SEQ ID NO: 2) were designed according to the sequences of chick ovoinhibitor exon 16 (Genbank Accession No: M16141) and a fragment of the chick ovomucoid promoter region (Genbank Accession No: J00897) respectively. The template DNA for PCR amplification of the ovomucoid promoter region was prepared from white leghorn chick blood.

Figure 2:
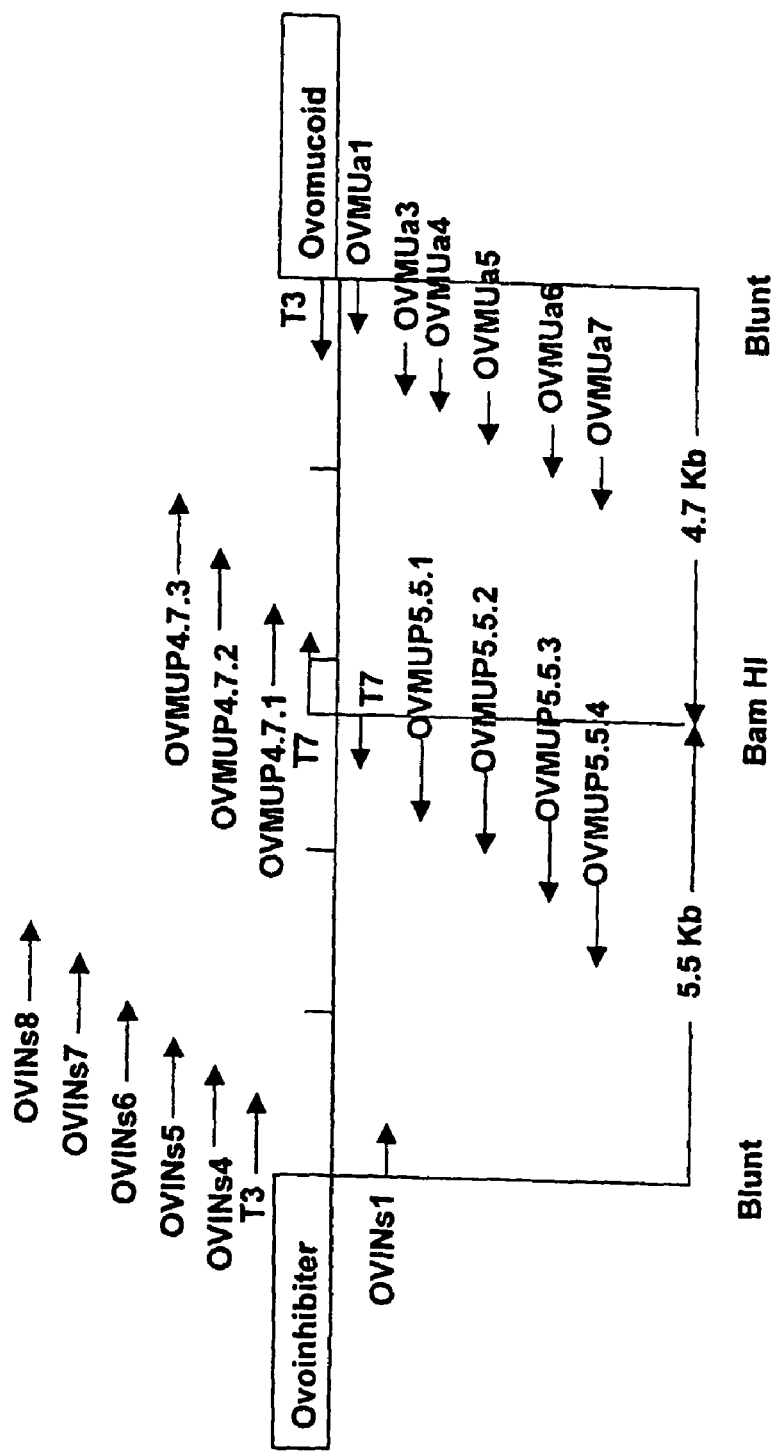
FIG. 2 illustrates the approximately 10 kb nucleic acid region that is 5' upstream of the chicken ovomucoid transcription start site, and the positions and orientations of primers used to sequence this region.

A series of different PCR conditions were carried out to optimize synthesis of the approximately 10.0 kb product, the results of which are shown in FIG. 2. In these tests, the template DNA concentrations were 500 ng, 100 ng, 50 ng, or 10 ng. Two sets of primers, OVINs1 (SEQ ID NO: 3) and OVMUa1 (SEQ ID NO: 4), or OVINs2 (SEQ ID NO: 1) and OVMUa2 (SEQ ID NO: 2) shown in FIG. 3, three $Mg^{++}$ concentrations (1.0 mM, 1.5 mM and 2.0 mM) and annealing temperatures from 50° C. to 70° C. were used.

The results of the tests were as shown in FIG. 2. As shown in lanes 1 through 8, test reactions having 500 ng DNA template, the OVINs1 (SEQ ID NO: 3) and OVMUa1 (SEQ ID NO: 4) primers, 60 mM Tris-$SO_4$, pH9.1, 18 mM $(NH_4)_2SO_4$, 1.0 mM $Mg^{2+}$, and annealing temperatures between 50° C. to 58° C. gave no specific DNA product. Also, as shown in lanes 17 through 24 of FIG. 2, in test reactions having 100 ng DNA template, the OVINs1 and OVMUa1 primers, 60 mM Tris-$SO_4$, pH9.1, 18 mM $(NH_4)_2SO_4$, 1.0 mM $Mg^{2+}$, and annealing temperatures between 50° C. to 58° C., no specific bands were seen. However, as shown in lanes 9 through 16 of FIG. 2, test reactions having 500 ng DNA template, the OVINs2 (SEQ ID NO: 1) and OVMUa2 (SEQ ID NO: 2) primers, 60 mM Tris-$SO_4$, pH9.1, 18 mM $(NH_4)_2SO_4$, 2 mM $Mg^{2+}$ and annealing temperatures between 60° C. to 68° C. have the band of the desired length of approximately 10 kb. As shown in lanes 25 through 32, reaction conditions containing 100 ng DNA template, the OVINs2 (SEQ ID NO: 1) and OVMUa2 (SEQ ID NO: 2) primers, 60 mM Tris-$SO_4$, pH9.1, 18 mM $(NH_4)_2SO_4$, 2 mM $Mg^{2+}$ and annealing temperatures between about 60° C. to about 68° C. gave an increased yield of the desired product.

An approximately 10 kb product was, therefore, detected when the following conditions were used: the optimum DNA template concentration was between about 50 ng to 500 ng; the primers were OVINs2 (SEQ ID NO: 1) and OVMUa2 (SEQ ID NO: 2); the $Mg^{2+}$ concentration was 2 mM; the annealing temperature was at or between about 60° C. to about 68° C. Each 50 µl PCR reaction consisted of 50 ng or 100 ng of template DNA, 0.1 µg each primer, 5 µl buffer B (from Elongase Enzyme Mix kit, Invitrogen Corp., Carlsbad, Calif.), 1 ml of 10 µM dNTP solution, and distilled deionized water. The PCR protocol was one cycle at 94° C. for 30 secs; thirty cycles at 94° C. for 30 secs, 60° C. for 30 secs and 68° C. for 10 mins. One cycle was performed at 68° C. for 10 mins, 35° C. for 30 mins with a final hold at 4° C. The PCR products were examined by 0.65% agarose gel analysis.

EXAMPLE 2

Cloning of PCR Products.

The PCR products were purified by standard methods. Briefly, PCI (phenol: chloroform: isoamyl alcohol, 24:25:1) and chloroform extraction were performed once. The DNA was precipitated by adding 3M sodium acetate pH5.2 to a final concentration of 0.3M together with 2.5 volumes of 100% ethanol. The DNA pellet was dried and dissolved in distilled deionized water and then sequenced on a ABI3700 automatic sequencer (Applied Biosystems, Foster City, Calif.) using the primers OVINs2 (SEQ ID NO: 1) and OVMUa2 (SEQ ID NO: 2) to confirm the identity of each PCR product. After confirmation of the identities, the approximately 10 kb PCR product was treated with T4 polynucleotide kinase to add a phosphate to the 5' end. Mung bean nuclease removed any overhanging adenines from the ends of the PCR products, thereby producing a blunt end. The PCR product was purified by PCI and chloroform extraction and precipitated by standard methods. This 10 kb product was then cleaved with Bam HI to give two fragments, of about 4.7 and about 5.5 kb respectively.

The vector plasmid pBluescript II KS (+/−) was cut by Bam HI and Eco RV and treated with calf intestinal alkaline phosphatase. DNA fragments to be ligated into the vector were analyzed by agarose gel electrophoresis and purified from agarose gel slices using a NucleoTrap Nucleic Acid Purification Kit (BD Biosciences Clontech, Palo Alto, Calif.). Fragments of 4.7 kb and 5.5 kb were inserted into the Bam HI/Eco RV-treated pBluescript to give the constructs pBS-OVMUP4.7 and pBS-OVMUP5.5 respectively.

Positive clones were screened by Xba I/Xho I digestion. Clone pBS-OVMUP4.7, gave fragments of about 4.7 kb and 2.96 kb. Clone pBS-OVMUP5.5 gave fragments of about 5.5 kb and 2.96 kb. Apparent positive clones having the 4.7 kb insert were further confirmed by Xba I/Hind III digestion that gave three fragments of 0.5 kb, 4.2 kb and 2.9 kb. The apparent positive clones with an insert of about 5.5 kb insert were further confirmed by Xba I/Kpn I digestion that gave three fragments of 2 kb, 3.5 kb and 2.96 kb.

A construct, pBS-OVMUP-10, containing the entire 10 kb PCR product cloned into the pBluescript KS II (+/−) vector was made by taking a 4.7 kb Bam HI/Xho I fragment from the pBS-OVMUP4.7 plasmid and inserting it into the Bam HI/Aba I cleaved sites of pBS-OVMUP5.5. The Xho I and Xba I cut ends were blunt-ended by treating the digested fragments with Klenow enzyme and dNTPs at 25° C. for 15 mins before the digestion with Bam HI.

EXAMPLE 3

Sequencing

Figure 1:
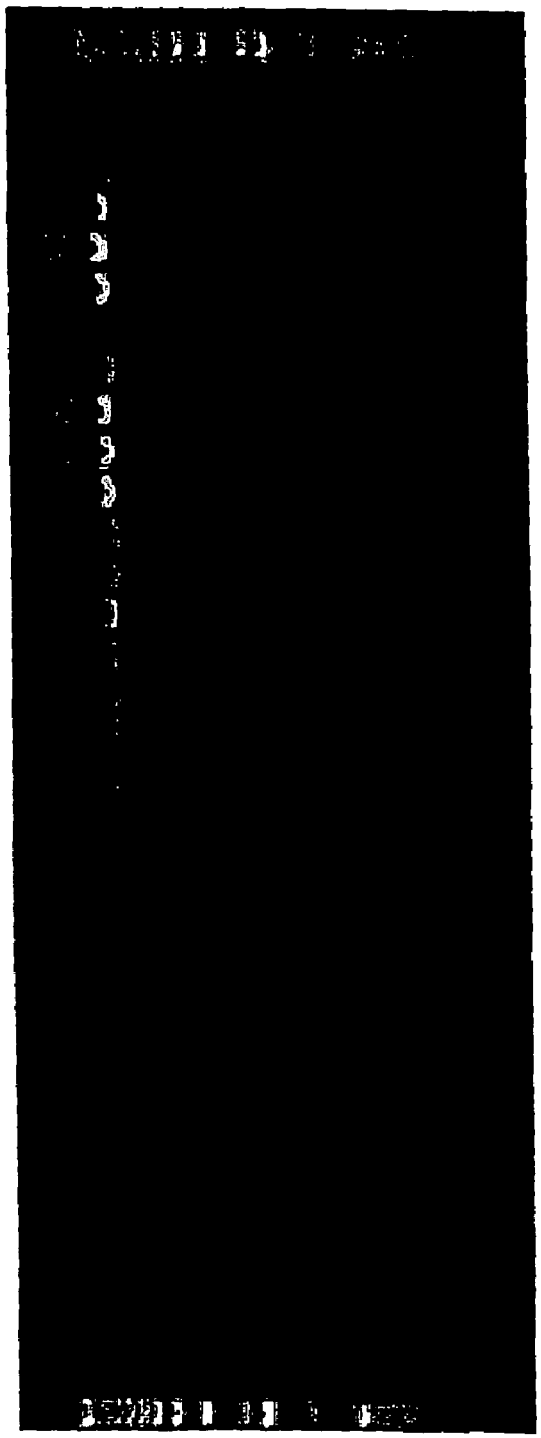
FIG. 1 illustrates an agarose gel analysis of PCR products from PCR amplification of chicken genomic DNA using the primers OVINs2 (SEQ ID NO: 1) and OVMUa2 (SEQ ID NO: 2).

The plasmids pBS-OVMUP4.7 and pBS-OVMUP5.5 were sequenced from both ends of each insert as shown in FIG. 1. The initial primers were T7 and T3 having the nucleic acid sequences 5'-TAATACGACTCACTATAGGG-3' (SEQ ID NO: 5) and 5'-ATTAACCCTCACTAAAGGGA-3' (SEQ ID NO: 6) respectively. Subsequent primers (SEQ ID NOS: 7-25), as shown in FIG. 3, were designed according to the sequence results as they became available. The approximately 10 kb sequence was edited and assembled by the ContigExpress software of the Vector NTI Suite, version 6.0 (InforMax, Inc.). The region of the approximately 10 kb PCR product described in Example 1 above that encompassed the Barn HI junction was sequenced using the primers OVMUa9 (SEQ ID NO 27) and OVINs9 (SEQ ID NO 28) (shown in FIG. 3).

Each sequence chromatogram was visually checked for sequence accuracy and to locate base ambiguities. Regions containing ambiguous bases were re-sequenced with the same primer or, if still ambiguous, with a new primer designed to sequence the complementary strand. Sequencing of the original 10 kb PCR fragment using the primers OVMUa9 (SEQ ID NO 27) and OVINs9 (SEQ ID NO 28) showed that the subcloned inserts of the plasmids pBS-OVMUP4.7 and pBS-OVMUP5.5 included all of the nucleic acid sequence of the parent fragment and no intervening Bam HI-Bam HI fragments were included in the final sequence SEQ ID NO: 26. The sequence (SEQ ID NO: 26) of the region lying between the 3' end of the ovoinhibitor gene and the transcription start site of the ovomucoid-encoding region is shown in FIG. 4.

EXAMPLE 4

Expression in Transfected Cultured Avian Myeloid and Oviduct Cells of Luciferase Regulated by the 10 kb Ovomucoid Promoter Construction of p10-OM-luc To facilitate insertion of coding sequences behind the ovomucoid promoter and in frame with the second ATG of the ovomucoid coding sequence, the Nco I site which overlaps the second ATG was changed to a Pci I site as depicted below. On the top is the wild type ovomucoid sequence at the start site of translation. On the bottom, the second Nco I site was changed to a Pci I site.

```
          Nco I Nco I

MetAlaMet
      CTCACCATGGCCATGGC           (SEQ ID NO: 32)

GAGTGGTACCGGTACCG           (SEQ ID NO: 33)

Nco I Pci I

MetAspMet
      CTCACCATGGACATGGA           (SEQ ID NO: 34)

GAGTGGTACCGGTACCG           (SEQ ID NO: 35)
```

The Pci I site in the Bluescript backbone of pBS-OVMUP-10 was destroyed by cutting with Pci I, filling in the ends with Klenow polymerase and religating, creating pOM-10-alpha. The proximal promoter region was PCR amplified with primers OM-5 (SEQ ID NO.:29) and OM-6 (SEQ ID NO.:30) and template pBS-OVMUP-10. The resulting PCR product (SEQ ID NO.:31) was cut with Not I and Tth111 I and cloned into the 12059 bp Not I-Tth111 I fragment of pOM-10-alpha, thereby creating pOM-10-Pci. The 1964 Nco I-S1-treated Kpn I frament of gWiz-luciferase (Gene Therapy Systems, Inc., San Diego, Calif.) was cloned into the 12824 Pci I-Sma I fragment of pOM-10-Pci, creating p10-OM-luc.

```
Primer sequences
OM-5
5'-GCGCGGCCGCCCGGGACATGTCCATGGTGA    (SEQ ID NO: 29)

GAGTACTGCCC-3'

OM-6
5'-GGCCCGGGATTCGCTTAACTGTGACTAGG-    (SEQ ID NO: 30)

3'

PCR product
GCGCGGCCGCCCGGGACATGTCCATGGTGAGAG    (SEQ ID NO: 31)

TACTGCCCGGCTCTGCAGGCGGCTGCCGGTGCT

CTGCTCCTGAGATGGTCCCCCCGAGGCTGCCTG

CAAATATATACAAACGTGGCGTCCGAACTGTTG

GACTGGAACACGGAGCAGCCAGCTGAATCTGTC

AGCGGCACAATGAGGCTGGTAATATTTATTGAG
```

```
                    -continued
GTCCTGACCTCCAGGTAATGGTCTGCGTCTCCC

AGGCAATTGATTTTGGCTGGACACTTGGTTAAT

AGCTTGAGACAAGTGTCACATGCTCTCAGTGGT

CAAAACCAAACAAACAGACTTTTGGACCAAAAA

AAAAAAAAACCTCTTAAGGACTCTGGTAGAACC

CTAAATAGCACAGAATGCTGAGGGGAGTAAGGG

ACAGGTCCTTCATTCGTCTCTGCATCCACATCT

CCCAGCAGGAAGCAGCTAAGGCTCAGCACCATC

GTGCCTGCAGCTCTGCTTTCCATGCAGTTCTGC

ATTCTTGGATATTCACCTCTAGGTAAAAGCACA

GGCCAGGGAGGCTTTGTCACCAGCAGAACTGAC

CAACCACTGCCAGGTGAAGCTGGCAGCACCGTA

TCTAACCTATGAAGTTAATGGTATTTAGCACTA

GCTTGATAAAAGGAAGGGTTTCTTGGCGGTTTC

ACTGCTTAAGTATAGAAGAGCTTGGTAGAAGAC

TTGAAAGCAAGGTAAATGCTGTCAAATACCACT

AAAAATGTCACTTGAACCTTATCAGCAGGGAGC

ACTTATTTACAGACCTAGTCACAGTTAAGCGAA

TTCCCGGGCC
```

The $1^{st}$ and $2^{nd}$ ATGs of the ovomucoid sequence are shown underlined. Note that the ovomucoid coding sequence is in reverse. The underlined, bold A is not in the wildtype sequence but was incorporated into pOM-10-Pci due to a error in the oligo OM-5.

Expression of Luciferase

For expression in avian cells of non-magnum origin, HD11 cells, a chicken myeloid cell line was used. Cells were cultured as described in Beug, H., et al. (Chicken hematopoietic cells transformed by seven strains of defective avian leukemia viruses display three distinct phenotypes of differentiation. (1979) Cell, 18: 375-90, in which these cells were referred to as HBCI cells), herein incorporated by reference in its entirety. Plasmid DNA was transfected into HD11 cells with Lipofectamine 2000 (Invitrogen Corporation, Carlsbad, Calif.) according to the manufacturer's instructions.

48 hours post-transfection, the cells were harvested and pelleted. The supernatant was removed and 20 µl of 10 mM Tris, pH 7.8, 1 mM EDTA (TE) was added. The cells were frozen at −80° C. and thawed. 5 µl of the cell suspension was mixed with 25 µl of Bright-Glo™ reagent (Bright-Glo™ Luciferase Assay System, Promega, Madison, Wis. and relative light units per second measured on a Berthold Detection Systems (Oak Ridge, Tenn.) FB12 luminometer.

Results are depicted in FIG. 6A. HD11 cells are permissive for the CMV promoter and should be able to only weakly activate the ovomucoid promoter. Some expression of the luciferase gene linked to the 10 kb ovomucoid is evident.

For expression in avian oviduct cells, primary tubular gland cells were isolated as follows. The oviduct of a Japanese quail (Coturnix coturnix japonica) was removed and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and triturating for 30 minutes at 37° C. The cell suspension was then filtered through sterile surgical gauze, washed three times with F-12 medium (Life Technologies, Grand Island, N.Y.) by centrifugation at 200×g, and resuspended in OPTIMEM™ (Life Technologies) such that the $OD_{600}$ was approximately 2. 800 µl of the cell suspension was plated in each well of a 6-well dish. For each transfection, 4.0 µl of DMRIE-C liposomes (Life Technologies) and 2.0 µg of plasmid DNA was preincubated for 15 minutes at room temperature in 200 µl of OPTIMEM™, and then added to the oviduct cells. Cells with DNA/liposomes were incubated for about 5 hours at 37° C. in 5% $CO_2$. Next, 2.0 ml of DMEM (Life Technologies), supplemented with 15% fetal bovine serum (FBS) (Atlanta Biologicals, Atlanta, Ga.), 2×penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours. Medium was then harvested and centrifuged at 110×g for 5 minutes.

For quantitation, the cells were scraped into the media with a rubber policeman. One milliliter was transferred to an eppendorf tube and the cells pelleted. The supernatant was removed and 20 µl of 10 mM Tris, ph 7.8, 1 mM EDTA (TE) was added. The cells were frozen at −80° C. and thawed. 5 µl of the cell suspension was mixed with 25 µl of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

The results are depicted in FIG. 6B. Expression of luciferase is evident from the CMV and 10 kb ovomucoid promoters. The ovomucoid promoter has more activity relative to the CMV promoter in the tubular gland cells (ratio of CMV to ovomucoid is 152) than in the HD11 cells (ratio of CMV to ovomucoid is 2221).

EXAMPLE 5

Expression in Transfected Cultured Avian Oviduct Cells of Human Interferon α2b Regulated by the 10 kb Ovomucoid Promoter Construction of p10-OM-IFN The CMV promoter region of pAVIJCR-A137.91.1.2 flanked by Nco I sites (pCMV-human IFN-alpha-2b-MagMax) was replaced with the 1051 bp Nco I-Nco I fragment from pBS-OVMUP-4.4, thereby inserting the 1 kb ovomucoid promoter in front of the IFN coding sequence and SV40 polyadenylation signal and creating p1kb-OM-IFNMM. A 1816 bp Cla I-Sac I fragment of p1kb-OM-IFNMM was inserted into the 6245 bp Cla I-Sac I fragment of pBS-OVMUP-4.4, thereby fusing the 4.4 kb ovomucoid fragment with the IFN coding sequence and creating p4.4OM-IFNMM. The 8511 bp BamH I-Sal I fragment of pBS-OVMUP-10 was ligated to the 5148 bp BamH I-Sal I fragment of p4.4OM-IFN, thereby placing the 10 kb ovomucoid promoter in front of the IFN coding sequence, creating p10-OM-IFN.

Expression of Interferon

Quail primary tubular gland cells were isolated and treated as described in Example 4. 100 µl of supernatants were analyzed by ELISA (PBL Biomedical Laboratories, Flanders, N.J.) for human interferon α2b content. The results are depicted in FIG. 7. Expression of interferon is evident from the CMV and 10 kb ovomucoid promoters.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the fill scope of equivalents to which such claims are entitled.

What is claimed is:

1. A transgenic avian comprising a nucleic acid comprising an avian ovomucoid gene expression control region operably linked to a nucleotide sequence encoding a heterologous polypeptide, wherein the ovomucoid gene expression control region comprises a sequence at least 95% sequence identical to SEQ ID NO:26.

2. The transgenic avian of claim 1, wherein the avian is selected from the group consisting of a chicken, a turkey, a duck, a goose, a quail, a pheasant, a ratite, an ornamental bird and a feral bird.

3. The transgenic avian of claim 1, wherein the avian is a chicken.

4. The transgenic avian of claim 1, wherein the ovomucoid gene expression control region comprises the nucleic acid sequence of SEQ ID NO:26.

5. The transgenic avian of claim 1, wherein the nucleic acid comprises a polyadenylation signal sequence.

6. The transgenic avian of claim 5, wherein the polyadenylation signal sequence is derived from the SV40 virus.

7. The transgenic avian of claim 1, wherein the nucleotide sequence comprises a codon optimized for protein expression in an avian.

8. The transgenic avian of claim 1, wherein the heterologous polypeptide is a human pharmaceutical protein.

9. The trafisgenic avian of claim 1, wherein the transgenic avian produces the heterologous polypeptide in the serum or an egg white.

10. The transgenic avian of claim 9, wherein the transgenic avian produces the heterologous polypeptide in an egg white.

11. The transgenic avian of claim 10, wherein the nucleotide sequence encodes an immunoglobulin or subunit thereof.

12. The transgenic avian of claim 1, wherein the heterologous polypeptide is a member selected from the group consisting of human growth hormone, interferon, lysozyme, β-casein, albumin, α-1 antitrypsin, antithrombin III, collagen, factor VIII, factor IX, factor X, fibrinogen, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, chymotrypsin, immunotoxins, and immunoglobulins.

* * * * *

```
                              SEQUENCE LISTING

<160> NUMBER OF SEQ ID NOS: 35

<210> SEQ ID NO 1
<211> LENGTH: 30
<212> TYPE: DNA
<213> ORGANISM: Artificial
<220> FEATURE:
<223> OTHER INFORMATION: Primer OVINs2

<400> SEQUENCE: 1
taggcagagc aataggactc tcaacctcgt                                        30

<210> SEQ ID NO 2
<211> LENGTH: 30
<212> TYPE: DNA
<213> ORGANISM: Artificial
<220> FEATURE:
<223> OTHER INFORMATION: Primer OVMa2

<400> SEQUENCE: 2
aagcttctgc agcactctgg gagttactca                                        30

<210> SEQ ID NO 3
<211> LENGTH: 20
<212> TYPE: DNA
<213> ORGANISM: Artificial
<220> FEATURE:
<223> OTHER INFORMATION: Primer OVINs1

<400> SEQUENCE: 3
gggaaacaat ctgccttgca                                                   20

<210> SEQ ID NO 4
<211> LENGTH: 21
<212> TYPE: DNA
<213> ORGANISM: Artificial
<220> FEATURE:
<223> OTHER INFORMATION: Primer OVMUa1

<400> SEQUENCE: 4
aagccacaaa gcacgaaaga g                                                 21

<210> SEQ ID NO 5
<211> LENGTH: 20
<212> TYPE: DNA
<213> ORGANISM: Artificial
<220> FEATURE:
<223> OTHER INFORMATION: Primer T3

<400> SEQUENCE: 5
taatacgact cactataggg                                                   20

<210> SEQ ID NO 6
<211> LENGTH: 20
```

```
<212> TYPE: DNA
<213> ORGANISM: Artificial
<220> FEATURE:
<223> OTHER INFORMATION: Primer T7

<400> SEQUENCE: 6
attaaccctc actaaaggga                                              20

<210> SEQ ID NO 7
<211> LENGTH: 20
<212> TYPE: DNA
<213> ORGANISM: Artificial
<220> FEATURE:
<223> OTHER INFORMATION: Primer OVINs4

<400> SEQUENCE: 7
agatgaggtg gatggtttac                                              20

<210> SEQ ID NO 8
<211> LENGTH: 20
<212> TYPE: DNA
<213> ORGANISM: Artificial
<220> FEATURE:
<223> OTHER INFORMATION: Primer OVINs5

<400> SEQUENCE: 8
cagcttctgc tagcgtaggt                                              20

<210> SEQ ID NO 9
<211> LENGTH: 20
<212> TYPE: DNA
<213> ORGANISM: Artificial
<220> FEATURE:
<223> OTHER INFORMATION: Primer OVINs6

<400> SEQUENCE: 9
acgtgaactc aaagaggcac                                              20

<210> SEQ ID NO 10
<211> LENGTH: 20
<212> TYPE: DNA
<213> ORGANISM: Artificial
<220> FEATURE:
<223> OTHER INFORMATION: Primer OVINs7

<400> SEQUENCE: 10
atctcctgag ctcggtgctt                                              20

<210> SEQ ID NO 11
<211> LENGTH: 20
<212> TYPE: DNA
<213> ORGANISM: Artificial
<220> FEATURE:
<223> OTHER INFORMATION: Primer OVINs8

<400> SEQUENCE: 11
acgaggttcc atgtctttca                                              20

<210> SEQ ID NO 12
<211> LENGTH: 31
<212> TYPE: DNA
<213> ORGANISM: Artificial
<220> FEATURE:
<223> OTHER INFORMATION: Primer OVMUa3

<400> SEQUENCE: 12
```

-continued

```
taaatagcac agaacgctga ggggagtaag g                                      31

<210> SEQ ID NO 13
<211> LENGTH: 20
<212> TYPE: DNA
<213> ORGANISM: Artificial
<220> FEATURE:
<223> OTHER INFORMATION: Primer OVMUa4

<400> SEQUENCE: 13
gaagagcttg gtagaagact                                                   20

<210> SEQ ID NO 14
<211> LENGTH: 21
<212> TYPE: DNA
<213> ORGANISM: Artificial
<220> FEATURE:
<223> OTHER INFORMATION: Primer OVMUa5

<400> SEQUENCE: 14
atggaaatat gggtttcctt c                                                 21

<210> SEQ ID NO 15
<211> LENGTH: 20
<212> TYPE: DNA
<213> ORGANISM: Artificial
<220> FEATURE:
<223> OTHER INFORMATION: Primer OVMUa6

<400> SEQUENCE: 15
gcagcttatg gctaatcgct                                                   20

<210> SEQ ID NO 16
<211> LENGTH: 20
<212> TYPE: DNA
<213> ORGANISM: Artificial
<220> FEATURE:
<223> OTHER INFORMATION: Primer OVMUa7

<400> SEQUENCE: 16
agtgaccact atctgacctg                                                   20

<210> SEQ ID NO 17
<211> LENGTH: 20
<212> TYPE: DNA
<213> ORGANISM: Artificial
<220> FEATURE:
<223> OTHER INFORMATION: Primer OVMUa8

<400> SEQUENCE: 17
taatcaggaa ggcacacagc                                                   20

<210> SEQ ID NO 18
<211> LENGTH: 20
<212> TYPE: DNA
<213> ORGANISM: Artificial
<220> FEATURE:
<223> OTHER INFORMATION: Primer OVMUP4.7.1

<400> SEQUENCE: 18
agatctggag cagcacttgt                                                   20

<210> SEQ ID NO 19
<211> LENGTH: 20
<212> TYPE: DNA
<213> ORGANISM: Artificial
```

```
<220> FEATURE:
<223> OTHER INFORMATION: Primer OVMUP4. 7. 2

<400> SEQUENCE: 19
agcatgaagt tcctcaccca                                               20

<210> SEQ ID NO 20
<211> LENGTH: 20
<212> TYPE: DNA
<213> ORGANISM: Artificial
<220> FEATURE:
<223> OTHER INFORMATION: Primer OVMUP4. 7. 3

<400> SEQUENCE: 20
atggagagga atattccctt                                               20

<210> SEQ ID NO 21
<211> LENGTH: 18
<212> TYPE: DNA
<213> ORGANISM: Artificial
<220> FEATURE:
<223> OTHER INFORMATION: Primer OVMUP4. 7. 4

<400> SEQUENCE: 21
atttctccag gcgtgtgg                                                 18

<210> SEQ ID NO 22
<211> LENGTH: 18
<212> TYPE: DNA
<213> ORGANISM: Artificial
<220> FEATURE:
<223> OTHER INFORMATION: Primer OVMUP5. 5. 1

<400> SEQUENCE: 22
atttctccag gcgtgtgg                                                 18

<210> SEQ ID NO 23
<211> LENGTH: 20
<212> TYPE: DNA
<213> ORGANISM: Artificial
<220> FEATURE:
<223> OTHER INFORMATION: Primer VMUP5. 5. 2

<400> SEQUENCE: 23
atgcgagtga aggagagttc                                               20

<210> SEQ ID NO 24
<211> LENGTH: 20
<212> TYPE: DNA
<213> ORGANISM: Artificial
<220> FEATURE:
<223> OTHER INFORMATION: Primer OVMUP5. 5. 3

<400> SEQUENCE: 24
gcagcacgtg taagcttgta                                               20

<210> SEQ ID NO 25
<211> LENGTH: 20
<212> TYPE: DNA
<213> ORGANISM: Artificial
<220> FEATURE:
<223> OTHER INFORMATION: Primer OVMUP5. 5. 4

<400> SEQUENCE: 25
caaggcaaat tatcagcaga                                               20
```

-continued

<210> SEQ ID NO 26
<211> LENGTH: 9980
<212> TYPE: DNA
<213> ORGANISM: Gallus gallus
<220> FEATURE:
<221> NAME/KEY: 3'UTR
<222> LOCATION: (1)..(255)
<223> OTHER INFORMATION: 3' untranslated region of ovoinhibitor
<220> FEATURE:
<221> NAME/KEY: misc_feature
<222> LOCATION: (2761)..(3024)
<223> OTHER INFORMATION: CR1-like element
<220> FEATURE:
<221> NAME/KEY: 5'UTR
<222> LOCATION: (9403)..(9920)
<223> OTHER INFORMATION: 5' untranslated region of ovomucoid

<400> SEQUENCE: 26

```
taggcagagc aataggactc tcaacctcgt gagtatggca gcatgttaac tctgcactgg      60
agtccagcgt gggaaacaat ctgccttgca catgagtctt cgtgggccaa tattccccaa     120
cggttttcct tcagcttgtc ttgtctccta agctctcaaa acaccttttt ggtgaataaa     180
ctcacttggc aacgtttatc tgtcttacct tagtgtcacg tttcatccct attcccttt      240
ctcctcctcc gtgtggtaca cagtggtgca cactggttct tctgttgatg ttctgctctg     300
acagccaatg tgggtaaagt tcttcctgcc acgtgtctgt gttgttttca cttcaaaaag     360
ggccctgggc tccccttgga gctctcaggc atttccttaa tcatcacagt cacgctggca     420
ggattagtcc ctcctaaacc ttagaatgac ctgaacgtgt gctccctctt tgtagtcagt     480
gcagggagac gtttgcctca agatcagggt ccatctcacc cacagggcca ttcccaagat     540
gaggtggatg gtttactctc acaaaaagtt ttcttatgtt tggctagaaa ggagaactca     600
ctgcctacct gtgaattccc ctagtcctgg ttctgctgcc actgctgcct gtgcagcctg     660
tcccatggag ggggcagcaa ctgctgtcac aaaggtgatc ccaccctgtc tccactgaaa     720
tgacctcagt gccacgtgtt gtatagggta taaagtacgg gaggggatg cccggctccc      780
ttcagggttg cagagcagaa gtgtctgtgt atagagtgtg tcttaatcta ttaatgtaac     840
agaacaactt cagtcctagt gttttgtggg ctggaattgc ccatgtggta gggacaggcc     900
tgctaaatca ctgcaatcgc ctatgttctg aaggtatttg ggaaagaaag ggatttgggg     960
gattgcctgt gattggcttt aattgaatgg caaatcacag gaaagcagtt ctgctcaaca    1020
gttggttgtt tcagccaatt cttgcagcca aagagccggg tgcccagcga tataatagtt    1080
gtcacttgtg tctgtatgga tgacagggag gtagggtgac ctgaggacca ccctccagct    1140
tctgctagcg taggtacagt caccacctcc agctccacac gagtcccatc gtggtttacc    1200
aaagaaacac aattatttgg accagtttgg aaagtcaccc gctgaattgt gaggctagat    1260
taatagagct gaagagcaaa tgttcccaac ttggagatac tagttggtat tagtatcaga    1320
ggaacagggc catagcacct ccatgctatt agattccggc tggcatgtac ttttcaagat    1380
gatttgtaac taacaatggc ttattgtgct tgtcttaagt ctgtgtccta atgtaaatgt    1440
tcctttggtt tatataacct tcttgccatt tgctcttcag gtgttcttgc agaacactgg    1500
ctgctttaat ctagtttaac tgttgcttga ttattcttag ggataagatc tgaataaact    1560
ttttgtggct ttggcagact ttagcttggg cttagctccc acattagctt tgctgccttt    1620
ttctgtgaag ctatcaagat cctactcaat gacattagct gggtgcaggt gtaccaaatc    1680
ctgctctgtg gaacacattg tctgatgata ccgaaggcaa acgtgaactc aaagaggcac    1740
agagttaaga agaagtctgt gcaattcaga ggaaaagcca aagtggccat tagacacact    1800
```

-continued

```
ttccatgcag catttgccag taggtttcat ataaaactac aaaatggaat aaaccactac    1860
aaatgggaaa agcctgatac tagaatttaa atattcaccc aggctcaagg ggtgtttcat    1920
ggagtaatat cactctataa aagtagggca gccaattatt cacagacaaa gctttttttt    1980
ttctgtgctg cagtgctgtt tttcggctga tccagggtta cttattgtgg gtctgagagc    2040
tgaatgattt ctccttgtgt catgttggtg aaggagatat ggccagggg agatgagcat      2100 gttcaagagg aaacgttgca ttttggtggc ttgggagaaa ggtagaacga tatcaggtcc    2160
atagtgtcac taagagatct gaaggatggt tttacagaac agttgacttg gctgggtgca    2220
ggcttggctg taaatggatg gaaggatgga cagatgggtg gacagagatt tctgtgcagg    2280
agatcatctc ctgagctcgg tgcttgacag actgcagatc catcccataa ccttctccag    2340
catgagagcg cggggagctt tggtactgtt cagtctgctg cttgttgctt cctgggtgca    2400
cagtggtgat tttcttactc acacagggca aaaacctgag cagcttcaaa gtgaacaggt    2460
tgctctcata ggccattcag ttgtcaagat gaggtttttg gtttcttgtt ttgtaaggtg    2520
ggaagaagca ctgaaggatc agttgcgagg gcagggggttt agcactgttc agagaagtct    2580
tattttaact cctctcatga acaaaaagag atgcaggtgc agattctggc aagcatgcag    2640
tgaaggagaa agccctgaat ttctgatata tgtgcaatgt tgggcaccta acattccccg    2700
ctgaagcaca gcagctccag ctccatgcag tactcacagc tggtgcagcc ctcggctcca    2760
gggtctgagc agtgctggga ctcacgaggt tccatgtctt tcacactgat aatggtccaa    2820
tttctggaat gggtgcccat ccttggaggt ccccaaggcc aggctggctg cgtctccgag    2880
cagcccgatc tggtggtgag tagccagccc atggcaggag ttagagcctg atggtcttta    2940
aggtcccttc caacctaagc catcctacga ttctaggaat catgacttgt gagtgtgtat    3000
tgcagaggca atattttaaa gttataaatg ttttctcccc ttccttgttt gtcaaagtta    3060
tcttgatcgc cttatcaatg cttttggagt ctccagtcat ttttcttaca mcaaaaagag    3120
gaggaagaat gaagagaatc atttaatttc ttgattgaat agtaggattc agaaagctgt    3180
acgtaatgcc gtctctttgt atcgagctgt aaggtttctc atcatttatc agcgtggtac    3240
atatcagcac ttttccatct gatgtggaaa aaaaaatcct tatcatctac agtctctgta    3300
cctaaacatc gctcagactc tttaccaaaa aagctatagg ttttaaaact acatctgctg    3360
ataatttgcc ttgttttagc tcttcttcca tatgctgcgt ttgtgagagg tgcgtggatg    3420
ggcctaaact ctcagctgct gagcttgatg ggtgcttaag aatgaagcac tcactgctga    3480
aactgttttc atttcacagg aatgttttag tggcattgtt tttataacta catattcctc    3540
agataaatga aatccagaaa taattatgca aactcactgc atccgttgca caggtctttta  3600 tctgctagca aaggaaataa tttggggatg gcaaaaacat tccttcagac atctatattt    3660
aaaggaatat aatcctggta cccacccact tcatccctca ttatgttcac actcagagat    3720
actcattctc ttgttgttat catttgatag cgttttcttt ggttctttgc cacgctctgg    3780
gctatggctg cacgctctgc actgatcagc aagtagatgc gagggaagca gcagtgagag    3840
gggctgccct cagctggcac ccagccgctc agcctaggag gggaccttgc ctttccacca    3900
gctgaggtgc agccctacaa gcttacacgt gctgcgagca ggtgagcaaa gggagtcttc    3960
atggtgtgtt tcttgctgcc cggaagcaaa actttacttt cattcattcc ccttgaagaa    4020
tgaggaatgt ttggaaacgg actgctttac gttcaatttc tctcttccct ttaaggctca    4080 gccagggggcc attgctgagg acggcatcgg ggccccctgg accaaatctg tggcacagat   4140
```

```
ggtttcactt acatcagtgg atgtgggatc tgcgcctgta atgtgtcctt ctgaaggaag    4200
gaacgtgcct tccaagtgcc agccccacag cccccagccc ctccctgtgc tgctccaatt    4260
catctcctct tcctccttct cccttttgctg tttgtgctcg ggtagaaatc atgaagattt    4320
agaagagaaa acaaaataac tggagtggaa acccaggtga tgcagttcat tcagctgtca    4380
taggtttgtc gttgctatag gtctgtatca gagatgctar caccactttg ctgtcggtgc    4440
ttaactcggg tgaactctcc ttcactcgca tcatttgcgg gccttattta catccccagc    4500
atccatcacc ctctgggaaa atgggcgcac tggatctcta atggaagact ttccctcttt    4560
cagagcctgt gggatgtgca gtgacaagaa acgtggaggg gctgagcagc agcactgccc    4620
ccagggagca ggagcggatg ccatcggtgg cagcatccca aatgatgtca gcggatgctg    4680
agcaggcagc ggacgaacgg acagaagcga tgcgtacacc ttctgttgac atggtatttg    4740
gcagcgattt aacactcgct tcctagtcct gctattctcc acaggctgca ttcaaatgaa    4800
cgaagggaag ggaggcaaaa agatgcaaaa tccgagacaa gcagcagaaa tatttcttcg    4860
ctacggaagc gtgcgcaaac aaccttctcc aacagcacca aagagcaca gcgtaacctt    4920
tttcaagacc agaaaaggaa attcacaaag cctctgtgga taccagcgcg ttcagctctc    4980
ctgatagcag atttcttgtc aggttgcgaa tggggtatgg tgccaggagg tgcagggacc    5040
atatgatcat atacagcaca gcagtcattg tgcatgtatt aatatatatt gagtagcagt    5100
gttactttgc caaagcaata gttcagagat gagtcctgct gcatacctct atcttaaaac    5160
taacttataa atagtaaaac cttctcagtt cagccacgtg ctcctctctg tcagcaccaa    5220
tggtgcttcg cctgcaccca gctgcaagga atcagcccgt gatctcatta acactcagct    5280
ctgcaggata aattagattg ttccactctc ttttgttgtt aattacgacg gaacaattgt    5340
tcagtgctga tggtcctaat tgtcagctac agaaaacgtc tccatgcagt tccttctgcg    5400
ccagcaaact gtccaggcta tagcaccgtg atgcatgcta cctctcactc catccttctt    5460
ctctttccca ccagggagag ctgtgtgttt tcactctcag ccactctgaa caataccaaa    5520
ctgctacgca ctgcctccct cggaaagaga atccccttgt tgcttttta tttacaggat    5580
ccttcttaaa aagcagacca tcattcactg caaacccaga gcttcatgcc tctccttcca    5640
caaccgaaaa cagccggctt catttgtctt ttttaaatgc tgtttttccag gtgaattttg    5700
gccagcgtgt tggctgagat ccaggagcac gtgtcagctt tctgctctca ttgctcctgt    5760
tctgcattgc ctcttttctgg ggtttccaag agggggggag actttgcgcg gggatgagat    5820
aatgcccctt ttcttagggt ggctgctggg cagcagagtg gctctgggtc actgtggcac    5880
caatgggagg caccagtggg ggtgtgtttt gtgcaggggg gaagcattca cagaatgggg    5940
ctgatcctga agcttgcagt ccaaggcttt gtctgtgtac ccagtgaaat ccttcctctg    6000
ttacataaag cccagatagg actcagaaat gtagtcattc cagccccccct cttcctcaga    6060
tctggagcag cacttgtttg cagccagtcc tccccaaaat gcacagacct cgccgagtgg    6120
agggagatgt aaacagcgaa ggttaattac ctccttgtca aaaacacttt gtggtccata    6180
gatgtttctg tcaatcttac aaaacagaac cgagaggcag cgagcactga agagcgtgtt    6240
cccatgctga gttaatgaga cttggcagct cgctgtgcag agatgatccc tgtgcttcat    6300
gggaggctgt aacctgtctc cccatcgcct tcacaccgca gtgctgtcct ggacacctca    6360
ccctccataa gctgtaggat gcagctgccc agggatcaag agacttttcc taaggctctt    6420
aggactcatc tttgccgctc agtagcgtgc agcaattact catcccaact atactgaatg    6480
ggtttctgcc agctctgctt gtttgtcaat aagcattttct tcattttgcc tctaagtttc    6540
```

```
tctcagcagc accgctctgg gtgacctgag tggccacctg gaacccgagg ggcacagcca   6600
ccacctccct gttgctgctg ctccagggac tcatgtgctg ctggatgggg ggaagcatga   6660
agttcctcac ccagacacct gggttgcaat ggctgcagcg tgctcttctt ggtatgcaga   6720
ttgtttccag ccattacttg tagaaatgtg ctgtggaagc cctttgtatc tctttctgtg   6780
gcccttcagc aaaagctgtg ggaaagctct gaggctgctt tcttgggtcg tggaggaatt   6840
gtatgttcct tctttaacaa aaattatcct taggagagag cactgtgcaa gcattgtgca   6900
cataaaacaa ttcaggttga aagggctctc tggaggtttc cagcctgact actgctcgaa   6960
gcaaggccag gttcaaagat ggctcaggat gctgtgtgcc ttcctgatta tctgtgccac   7020
caatggagga gattcacagc cactctgctt cccgtgccac tcatggagag gaatattccc   7080
ttatattcag atagaatgtt atcctttagc tcagccttcc ctataacccc atgagggagc   7140
tgcagatccc catactctcc ccttctctgg ggtgaaggcc gtgtccccca gccccccttc   7200
ccaccctgtg ccctaagcag cccgctggcc tctgctggat gtgtgcctat atgtcaatgc   7260
ctgtccttgc agtccagcct gggacattta attcatcacc agggtaatgt ggaactgtgt   7320
catcttcccc tgcagggtac aaagttctgc acggggtcct ttcggttcag gaaaaccttc   7380
actggtgcta cctgaatcaa gctctattta ataagttcat aagcacatgg atgtgttttc   7440
ctagagatac gttttaatgg tatcagtgat ttttatttgc tttgttgctt acttcaaaca   7500
gtgcctttgg gcaggaggtg agggacgggt ctgccgttgg ctctgcagtg atttctccag   7560
gcgtgtggct caggtcagat agtggtcact ctgtggccag aagaaggaca aagatggaaa   7620
ttgcagattg agtcacgtta agcaggcatc ttggagtgat ttgaggcagt ttcatgaaag   7680
agctacgacc acttattgtt gttttcccct tttacaacag aagttttcat caaaataacg   7740
tggcaaagcc caggaatgtt tgggaaaagt gtagttaaat gttttgtaat tcatttgtcg   7800
gagtgctacc agctaagaaa aaagtcctac ctttggtatg gtagtcctgc agagaataca   7860
acatcaatat tagtttggaa aaaaacacca ccaccaccag aaactgtaat ggaaaatgta   7920
aaccaagaaa ttccttgggt aagagagaaa ggatgtcgta tactggccaa gtcctgccca   7980
gctgtcagcc tgctgaccct ctgcagttca ggaccatgaa acgtggcact gtaagacgtg   8040
tccctgcct ttgcttgccc acagatctct gcccttgtgc tgactcctgc acacaagagc   8100
atttccctgt agccaaacag cgattagcca taagctgcac ctgactttga ggattaagag   8160
tttgcaatta agtggattgc agcaggagat cagtggcagg gttgcagatg aaatcctttt   8220
ctaggggtag ctaagggctg agcaacctgt cctacagcac aagccaaacc agccaagggt   8280
tttcctgtgc tgttcacaga ggcagggcca gctggagctg gaggaggttg tgctgggacc   8340
cttctccctg tgctgagaat ggagtgattt ctgggtgctg ttcctgtggc ttgcactgag   8400
cagctcaagg gagatcggtg ctcctcatgc agtgccaaaa ctcgtgtttg atgcagaaag   8460
atggatgtgc acctccctcc tgctaatgca gccgtgagct tatgaaggca atgagccctc   8520
agtgcagcag gagctgtagt gcactcctgt aggtgctagg gaaatctct ggttcccagg   8580
gatgcattca taagggcaat atatcttgag gctgcgccaa atctttctga aatattcatg   8640
cgtgttccct taatttatag aaacaaacac agcagaataa ttattccaat gcctcccctc   8700
gaaggaaacc catatttcca tgtagaaatg taacctatat acacacagcc atgctgcatc   8760
cttcagaacg tgccagtgct catctcccat ggcaaaatac tacaggtatt ctcactatgt   8820
tggacctgtg aaaggaacca tggtaagaaa cttcggttaa aggtatggct gcaaaactac   8880
```

```
tcataccaaa acagcagagc tccagacctc tcttaggaa agagccactt ggagagggat      8940
ggtgtgaagg ctggaggtga gagacagagc ctgtcccagt tttcctgtct ctattttctg      9000
aaacgtttgc aggaggaaag acaactgta cttcaggca tagctggtgc cctcacgtaa        9060
ataagttccc cgaacttctg tgtcatttgt tcttaagatg ctttggcaga acactttgag      9120
tcaattcgct taactgtgac taggtctgta ataagtgct ccctgctgat aaggttcaag       9180 tgacatttt agtggtattt gacagcattt accttgcttt caagtcttct accaagctct      9240
tctatactta agcagtgaaa ccgccaagaa acccttcctt ttatcaagct agtgctaaat      9300
accattaact tcataggtta gatacggtgc tgccagcttc acctggcagt ggttggtcag      9360
ttctgctggt gacaaagcct ccctggcctg tgctttttacc tagaggtgaa tatccaagaa    9420
tgcagaactg catggaaagc agagctgcag gcacgatggt gctgagcctt agctgcttcc     9480
tgctgggaga tgtggatgca gagacgaatg aaggacctgt cccttactcc cctcagcatt     9540
ctgtgctatt tagggttcta ccagagtcct taagaggttt ttttttttt tggtccaaaa      9600 gtctgtttgt ttggttttga ccactgagag catgtgacac ttgtctcaag ctattaacca     9660
agtgtccagc caaaatcaat tgcctgggag acgcagacca ttacctggag gtcaggacct     9720
caataaatat taccagcctc attgtgccgc tgacagattc agctggctgc tccgtgttcc     9780
agtccaacag ttcggacgcc acgtttgtat atatttgcag gcagcctcgg ggggaccatc     9840
tcaggagcag agcaccggca gccgcctgca gagccgggca gtactctcac catggccatg      9900
gcaggtgtct tcgtgctgtt ctctttcgtg ctttgtggct tcctcccagg tgagtaactc      9960
ccagagtgct gcagaagctt                                                   9980
```

```
<210> SEQ ID NO 27
<211> LENGTH: 20
<212> TYPE: DNA
<213> ORGANISM: Artificial
<220> FEATURE:
<223> OTHER INFORMATION: Primer OVMUa9

<400> SEQUENCE: 27
aaatgaagcc ggctgttttc                                                     20

<210> SEQ ID NO 28
<211> LENGTH: 20
<212> TYPE: DNA
<213> ORGANISM: Artificial
<220> FEATURE:
<223> OTHER INFORMATION: Primer OVINs9

<400> SEQUENCE: 28
ctctcagcca ctctgaacaa                                                     20

<210> SEQ ID NO 29
<211> LENGTH: 40
<212> TYPE: DNA
<213> ORGANISM: Artificial
<220> FEATURE:
<223> OTHER INFORMATION: Primer

<400> SEQUENCE: 29
gcgcggccgc ccgggacatg tccatggtga gagtactgcc                               40

<210> SEQ ID NO 30
<211> LENGTH: 29
<212> TYPE: DNA
<213> ORGANISM: Artificial
```

```
<220> FEATURE:
<223> OTHER INFORMATION: Primer

<400> SEQUENCE: 30
ggcccgggat cgcttaact gtgactagg                                          29

<210> SEQ ID NO 31
<211> LENGTH: 802
<212> TYPE: DNA
<213> ORGANISM: Artificial
<220> FEATURE:
<223> OTHER INFORMATION: primer

<400> SEQUENCE: 31
gcgcggccgc ccgggacatg tccatggtga gagtactgcc cggctctgca ggcggctgcc        60
ggtgctctgc tcctgagatg gtcccccga ggctgcctgc aaatatatac aaacgtggcg       120
tccgaactgt tggactggaa cacggagcag ccagctgaat ctgtcagcgg cacaatgagg      180
ctggtaatat ttattgaggt cctgacctcc aggtaatggt ctgcgtctcc caggcaattg      240
attttggctg acacttggt taatagcttg agacaagtgt cacatgctct cagtggtcaa       300
aaccaaacaa acagactttt ggaccaaaaa aaaaaaaaac ctcttaagga ctctggtaga      360
accctaaata gcacagaatg ctgaggggag taagggacag gtccttcatt cgtctctgca      420
tccacatctc ccagcaggaa gcagctaagg ctcagcacca tcgtgcctgc agctctgctt     480
tccatgcagt tctgcattct tggatattca cctctaggta aaagcacagg ccagggaggc    540
tttgtcacca gcagaactga ccaaccactg ccaggtgaag ctggcagcac cgtatctaac    600
ctatgaagtt aatggtattt agcactagct tgataaaagg aagggtttct tggcggtttc    660
actgcttaag tatagaagag cttggtgaaa gacttgaaag caaggtaaat gctgtcaaat    720
accactaaaa atgtcacttg aaccttatca gcagggagca cttatttaca gacctagtca    780
cagttaagcg aattcccggg cc                                              802

<210> SEQ ID NO 32
<211> LENGTH: 17
<212> TYPE: DNA
<213> ORGANISM: Artificial
<220> FEATURE:
<223> OTHER INFORMATION: Primer

<400> SEQUENCE: 32
ctccacatgg ccatggc                                                    17

<210> SEQ ID NO 33
<211> LENGTH: 17
<212> TYPE: DNA
<213> ORGANISM: Artificial
<220> FEATURE:
<223> OTHER INFORMATION: Primer

<400> SEQUENCE: 33
gagtggtacc ggtaccg                                                    17

<210> SEQ ID NO 34
<211> LENGTH: 17
<212> TYPE: DNA
<213> ORGANISM: Artificial
<220> FEATURE:
<223> OTHER INFORMATION: Primer

<400> SEQUENCE: 34
```

```
ctcaccatgg acatgga                                                17
```

<210> SEQ ID NO 35
<211> LENGTH: 17
<212> TYPE: DNA
<213> ORGANISM: Artificial
<220> FEATURE:
<223> OTHER INFORMATION: Primer

<400> SEQUENCE: 35

```
gagtggtacc ggtaccg                                                17
```